(12) United States Patent
Yokoyama et al.

(10) Patent No.: US 8,980,560 B2
(45) Date of Patent: Mar. 17, 2015

(54) METHOD FOR ANALYZING DNA METHYLATION

(75) Inventors: Seiya Yokoyama, Kagoshima (JP); Suguru Yonezawa, Kagoshima (JP)

(73) Assignee: Kagoshima University, Kagoshima (JP)

(*) Notice: Subject to any disclaimer, the term of this patent is extended or adjusted under 35 U.S.C. 154(b) by 0 days.

(21) Appl. No.: 13/641,923

(22) PCT Filed: Apr. 21, 2011

(86) PCT No.: PCT/JP2011/060339
§ 371 (c)(1),
(2), (4) Date: Oct. 18, 2012

(87) PCT Pub. No.: WO2011/132798
PCT Pub. Date: Oct. 27, 2011

(65) Prior Publication Data
US 2013/0045478 A1    Feb. 21, 2013

(30) Foreign Application Priority Data
Apr. 21, 2010 (JP) ................... 2010-098163

(51) Int. Cl.
*C12Q 1/68* (2006.01)

(52) U.S. Cl.
CPC .................... *C12Q 1/6827* (2013.01)
USPC ........................ 435/6.11; 435/6.12

(58) Field of Classification Search
CPC .. C12Q 1/6827; C12Q 1/6858; C12Q 1/6883; C12Q 1/6848; C12Q 1/6832; C12Q 1/683
See application file for complete search history.

(56) References Cited

U.S. PATENT DOCUMENTS

2004/0048275 A1* 3/2004 Guldberg ........................ 435/6

FOREIGN PATENT DOCUMENTS

WO       02/18649 A1    3/2002

OTHER PUBLICATIONS

Guldberg et al. (Detection of mutations in GC-rich DNA by bisulphite denaturing gradient gel electrophoresis, Nucleic Acids Research, 1998, vol. 26, No. 6, 1548-49).*
Clark et al. (High sensitivity mapping of methylated cytosines, Nucleic Acids Research, 1994, vol. 22, No. 15, 2990-2997).*
Derks et al. (Methylation-specific PCR unraveled, Cellular Oncology 26 (2004) 291-299).*
Guldberg, et al., "Detection of mutations in GC-rich DNA by bisulphite denaturing gradient gel electrophoresis," Nucleic Acids Research, 1998, vol. 26, No. 6, pp. 1548-1549, entire text.
Koga, et al., "I, Kan, Tandogan ni Okeru Kesseichu DNA Methylation Shindan no Kokoromi (Attempts of Diagnosis of DNA Methylation in Blood Serum in Gastric, Hepatic, and Bile Duct Cancer Cases)," Japanese Journal of Gastroenterology, 2005, vol. 102, Special Extra Issue Sokai, p. A189 (031), entire text.
Derks, S., et al: "Methylation-Specific PCR Unraveled", Cellular Oncology, IOS Press, London, GB, vol. 26. No. 5/06, Jan. 1, 2004, pp. 291-299.
Aggerholm, Anni, et al: "Extensive intra- and interindividual heterogeneity of p15INK4B methylation in acute myeloid leukemia", Cancer Research, vol. 59, No. 2, Jan. 15, 1999, pp. 436-441.
Dar Shabir, A., et al: "Nested PCR-denaturing gradient gel electrophoresis approach to determine the diversity of sulfate-reducing bacteria in complex microbial communities", Applied and Environmental Microbiology, vol. 71, No. 5, May 2005, pp. 2325-2330.
Guldberg, P., et al: "Detection of Mutations in GC-Rich DNA by Bisulphite Denaturing Gradient Gel Electrophoresis", Nucleic Acids Research, Information Retrieval Ltd, vol. 26, No. 6, Jan. 1, 1998.
Seiya Yokoyama, et al: "The application of methylation specific electrophoresis (MSE) to DNA methylation analysis of the 5' CpG island of mucin in cancer cells", BMC Cancer, vol. 12, No. 1, Feb. 14, 2012, p. 67.
online, (2001), [Nov. 14, 2014] <URL:http://www.jpo.go.jp/shiryou/s_sonota/hyoujun_gijutsu/kakusan/0056.html>.
online, (2001), [Nov. 14, 2014] <URL:http://www.jpo.go.jp/shiryou/s_sonota/hyoujun_gijutsu/kakusan/0051.html>.
JP Office Action corresponding JP Application No. 2012-511733, dated Nov. 25, 2014.

* cited by examiner

*Primary Examiner* — Christopher M Babic
*Assistant Examiner* — Aaron Priest
(74) *Attorney, Agent, or Firm* — Lucas & Mercanti, LLP

(57) ABSTRACT

This invention provides a method for efficiently detecting DNA methylation. The method for detecting DNA methylation comprises subjecting DNA to bisulfite treatment, subjecting DNA after bisulfite treatment to a first PCR, subjecting the resultant to nested PCR, and subjecting amplified DNA to denaturing gradient gel electrophoresis.

3 Claims, 23 Drawing Sheets

Fig. 1

-400
GGGAAGTGGAGTGGGAGAGATTAGGGGTGGGTTTTTGATTTGTTGTTGTATAGGATTTTG
ATTAGTTAGTTGGGTTTTTGTTTTTATTTTTATGTAGTGTTGTTGTTGAGGTAAAATTAGAGT
TTAGGGGTTTTAAGTTTAGATTGTTTTTTTTTTTTTTTGGAGTTAGGGAGTAGGAGTGGTTGG
TGAAAGGGGGAGGTTAGTTGGAGAATAAATGGGTAGTTAGGGGTTGAGTGATTAGA
    Primer 1-1
GTTTTTGTATTTTATTAGGAATGGTTGGGAGGAGGAGGAAGAGGTAGGAGGTAGG
                                                Primer 1-3
GGAGGGGGTGGGGTGGGGAGTGTTTATTTGTTATTTGTTGGGTGTTAGGGTGGGTGG
GTGGGGAGTGGGGGGGATTGGTATAAAGTGGTAGGGTAGGGTTGTGTTTGTTTTATTTTA
AGTAGTTAGTGTTTGTTGTTGAATTTGTTTTTTTTTTATTTATTTATTATTATGAT
                Primer 1-4
ATTGGGTATTTAGTGTTTTTTTTTTTGTTTAGGTGGTTTTTGTTTATAGGGGG
TATGAGGTGGGGAGTGGGGTTGTTT GTTTAGGTGGTTTTTGTGGTTTTTTGTGGGTT
                Primer 1-2
TTGTTTTTTG (SEQ ID NO: 2)
200

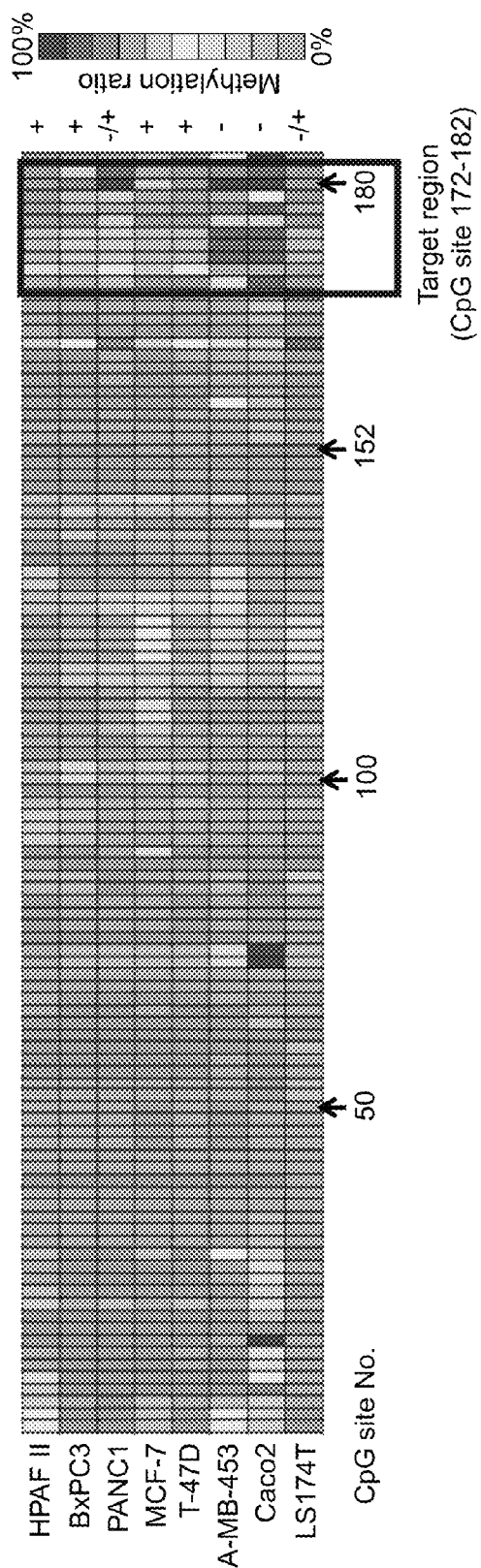
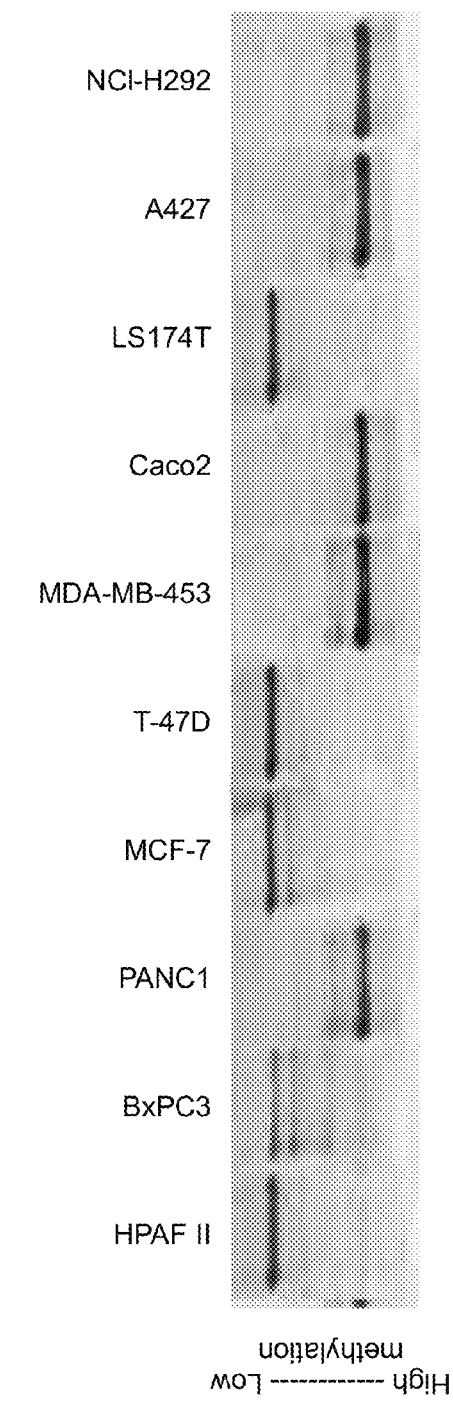
Fig. 2

Fig. 3

-500
GAAGGATTTTATATTTTTTTGTTTTGGGGAGGTTTTTTTGGGGGTTAGGTTTTGGAA
                                         Primer 2-1

GTTGTTTAGAGAGTTTGGGTTTTAGGAATGGGTTGGTTTTTAGTGTAATGTGAGTTTG
  Primer 2-3

ATTAGGTTTGGGGATTTGTTTAGTGGGTGTGTTTGGGGGTTATGGTGGGTTAAGGAGTT

TGATTAGAGATTTGTTTTTGGTAGGATATTTTTTTTGGTTATTTTTGGGTTTGTTTTTAG

TAGTTGTATGTGTTTTTGGGTGTGTGTTGGTATTTAGGTTATAGGGTTGTTTTATTTG
                                         Primer 2-4

AAGAAGGTTGTGTTTATTTAGGGAGTTATAAAGAGATGATTTTGATAATTTGAATTAAT
 Primer 2-2

ATTTTTTATTGGGGGTTTGGGTTTTGTAGTTGTTGTTTTTGATTATTGGTAGATGTTATA

TTTATTTTTGGTTTTTTTTGTTTTTTGTTTTTTATTTTTTGTTAGGATATATAAGGATT

AGATTTTGTTTTTGGGTG (SEQ ID NO: 7)
-1

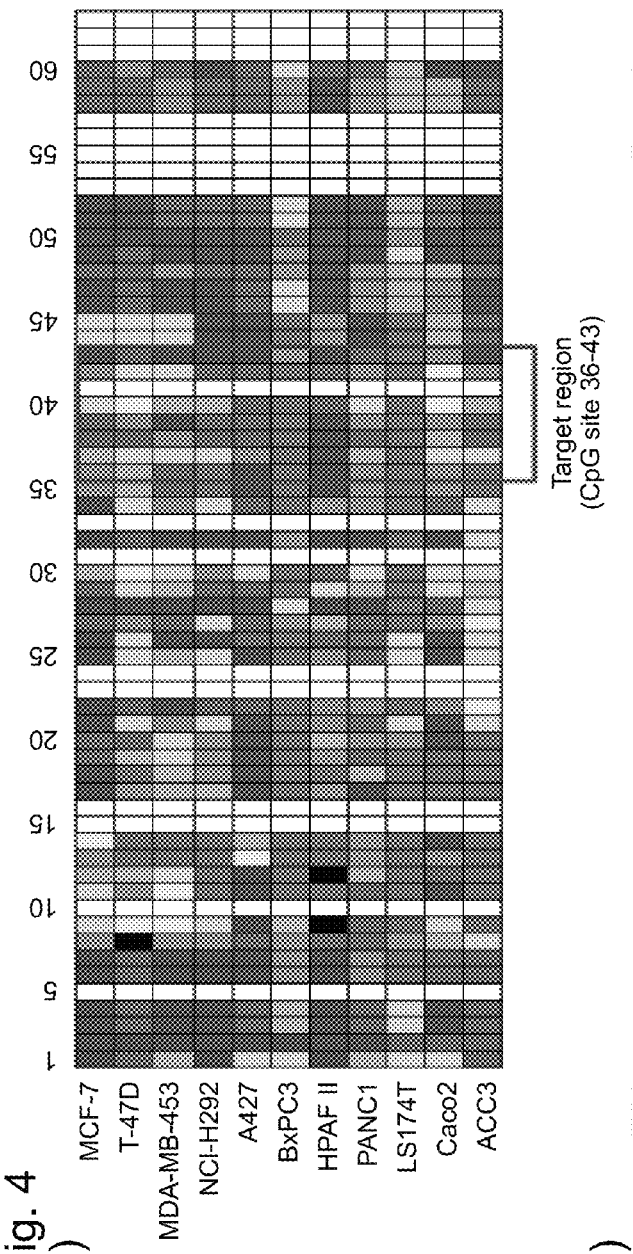
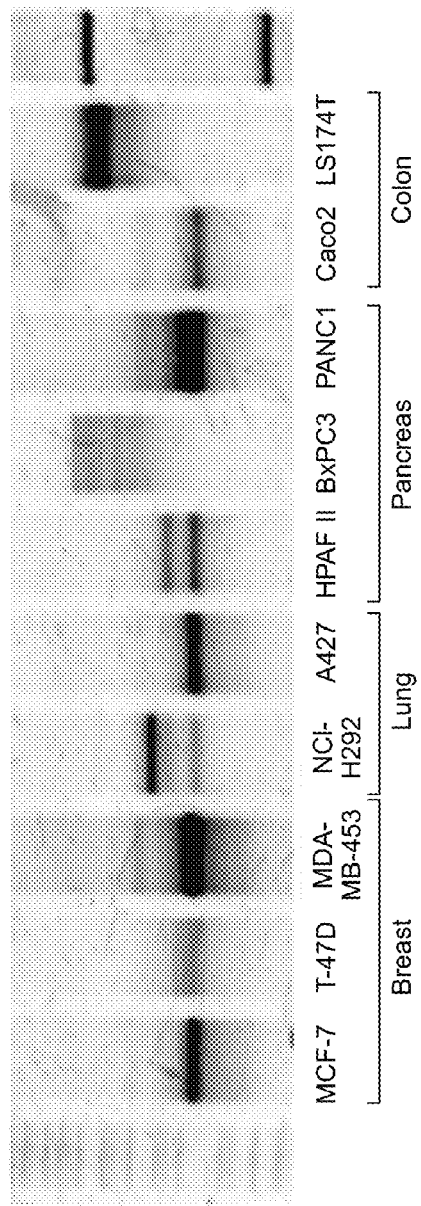
Fig. 4

Fig. 5

-250
TAGAGTAATGGGTGTATTGGTGTTTTTTTTTGGTGGGGTAGTGGGGTGGGGTTGA
                                              Primer 4-1

GGAGAGAAAGGGTGATTAGTGTGGGGTTTTGTTTTTTTTTTAGGTTTT
Primer 4-3

TGGTTTTTTGGAGAAATGTATTGGTTTGGGTAGTTGTTGAGGGGATGGGTTAT

GTTTGTTTTTATATTGTAGTTGTGGGTTGTGGAGTTTTTTAGGGAGTTAGGGGGAT

TTTTGTTGTAGTTATGAACGGGGTATGTTGGAGGAAGGGTTTTTTGGGTGTTTTTGAGT
                                        Primer 4-2
                                  Primer 4-4

TGTTTGTGTTTTTGTTTTTTTTGTATGTGGTTTTAGGTAAGTGATGGAGATA (SEQ ID NO: 12)
95

Fig. 13
(A) 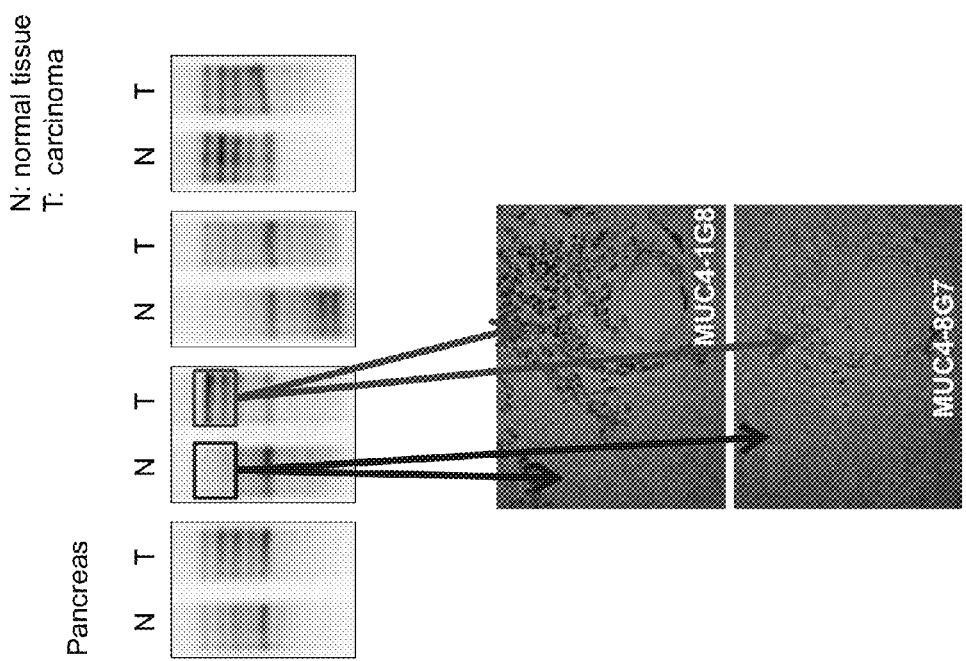
(B) 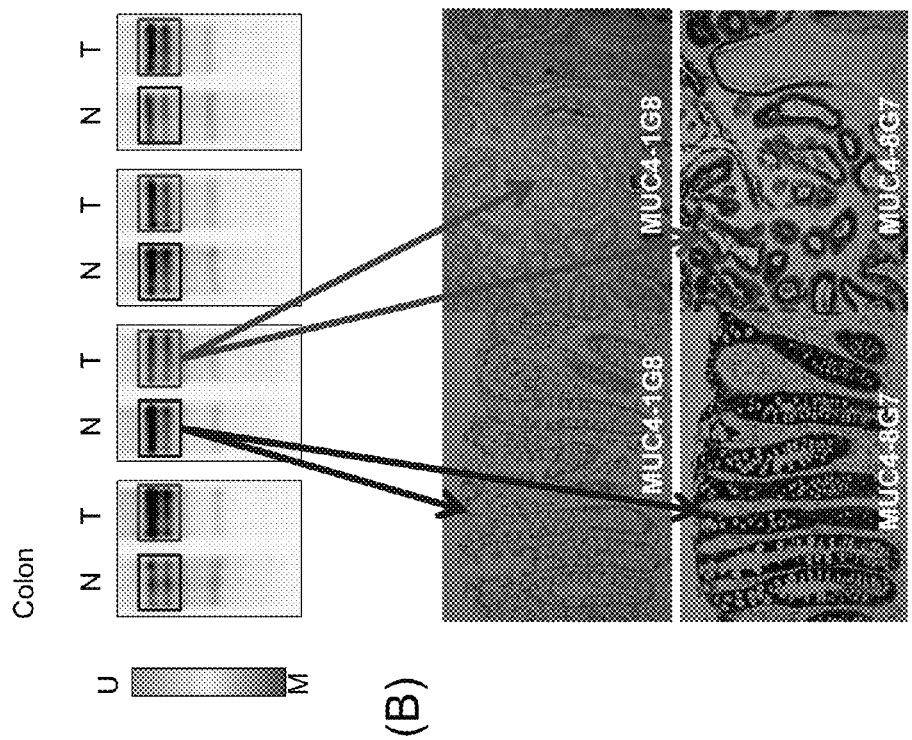

Fig. 18

(-4150 bp)TTAGGAGGTAGGTGGTTGTGTTATGGTTAGTTTGTTGTGTATTTTTGA
GAGTTTTTAGTAAGGTTGTAGTGATTATTTAGATTTTTTTTGAGGTTGTGGTGT
GGTTGGATTTTATTGTTTTGGGGATATATAGAAAATGTTTATAGAGTTTAGAAA
TAAGGTTTAGTGGGTTTTTGGAAAGTTTGGGTGTGTGGAGTTGGGGTTGTAG
                              Primer 5-1
GTTTTGGAATTGTAGGTATTGGTTTTTTGAGGTTTTTGGTTTGGTGGGGT
TTTTATGGGATTAGGTGGTTAGTTTGGTTTATGTTTAGGGGTTTTGGGTGTTG
                           Primer 5-3
AGTTTAGGTTTTAAGAGGAAGTTTAGTATAGTAGGGGTTATTAATATTGGTGGG
GGGAAGTTATTTTAGTTGGATTTTAGTAGTGGTTTTGGGTGATGTTGGTTGAGG
GAGGAGAAAGTTGTGGTTGGGTGGGTAAGGTTTGGGTGGTTAGTTGGTAGGTG
                           Primer 5-4
TTTTGGGGTTTGGTTTTAGTTTTAGATATGTAGGGGGTATTTTTTTGAGGGTTAT
GTTGGTGATTTAGATTGTTTAGAGGTTATGTATGGATTGGGTTAGTGATTTAGGT
TTGTTTTTGTTGGGGGTTGGATATTGATTATTTATTGTTTTTTGTTATTTGAGG
         Primer 5-2
GTTAAGGAGGGTAGGTTTTTAGGTATTTATAT (-3450 bp from origin of transcription) (SEQ ID NO: 29)

Fig. 19
(A) 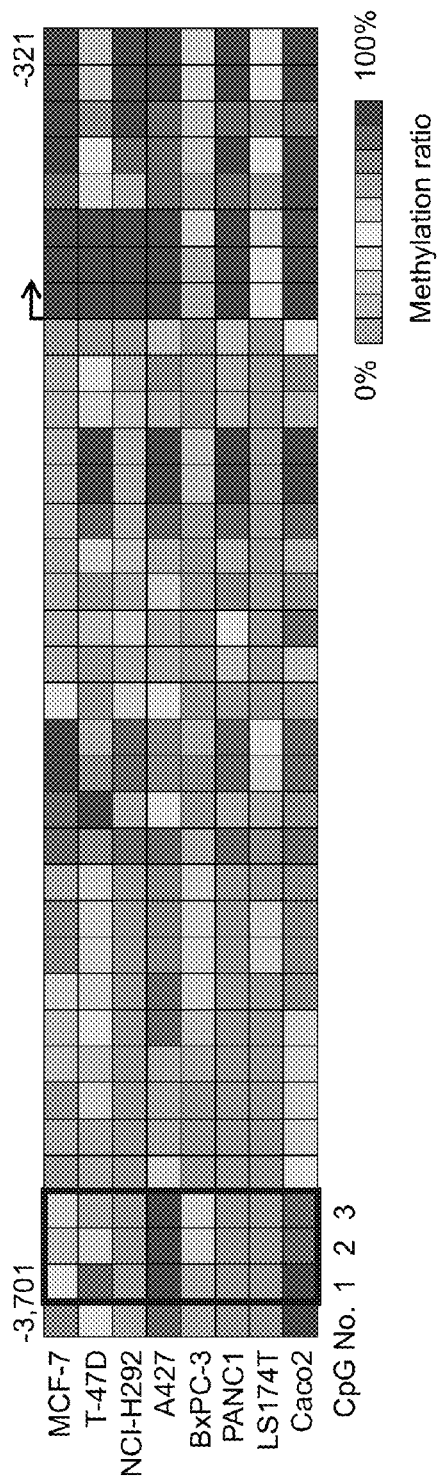
(B) 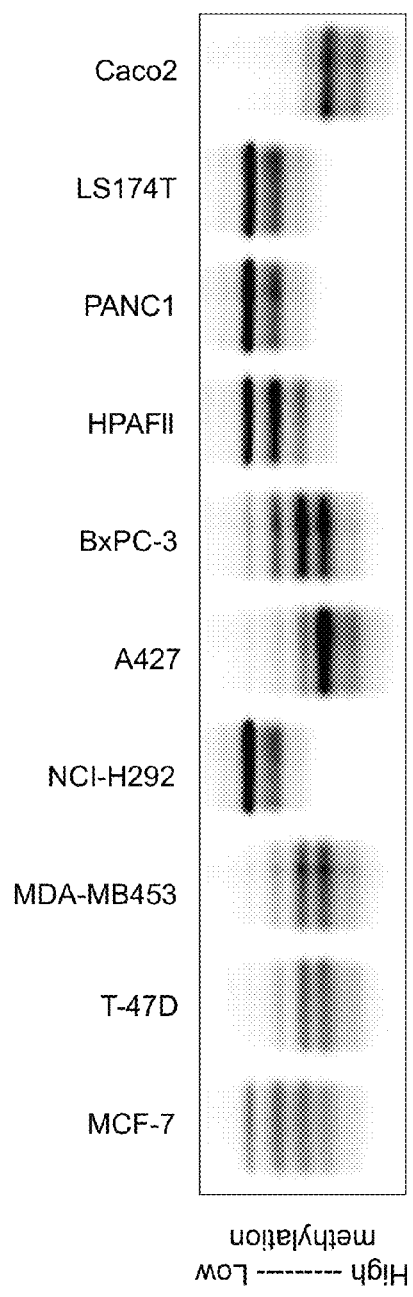

Fig. 22
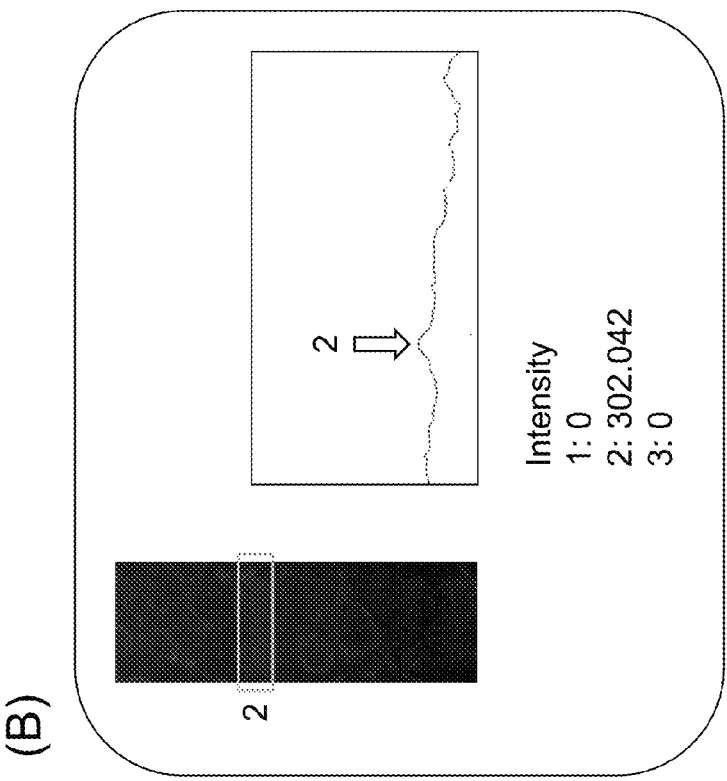
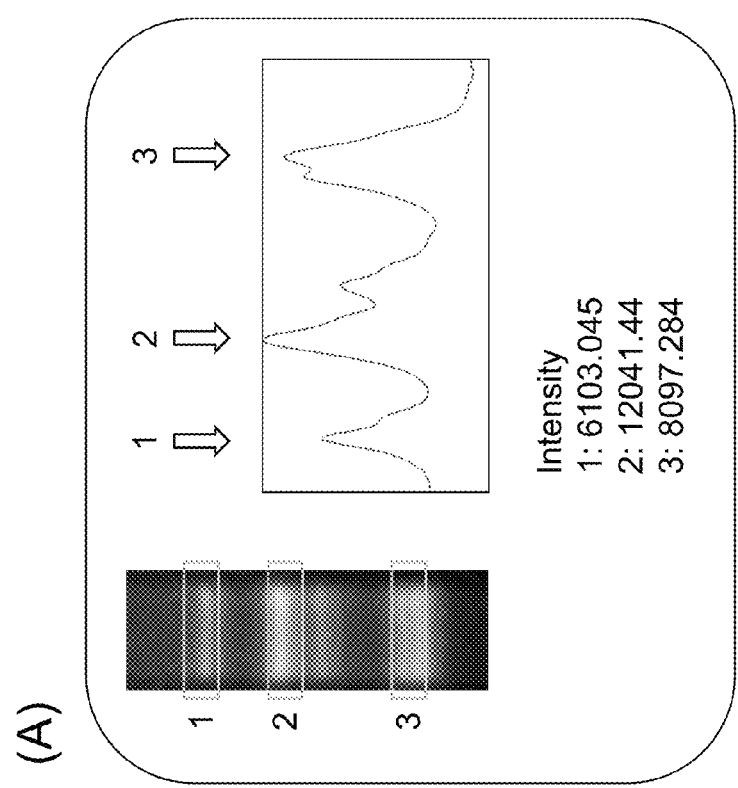

METHOD FOR ANALYZING DNA METHYLATION

CROSS-REFERENCE TO RELATED APPLICATIONS

This application is a 371 of PCT/JP2011/060339, filed Apr. 21, 2011, which claims the benefit of priority from Japanese Patent Application No. 2010-098163, filed Apr. 21, 2010, the contents of each of which are incorporated herein by reference.

TECHNICAL FIELD

The present invention relates to a method for detecting DNA methylation such as DNA methylation patterns and continuity, for example.

BACKGROUND ART

Epigenetics is a field of genetic or molecular biological research aimed at elucidation of the mechanisms of gene expression control that are not defined in terms of the genome. A major molecular mechanism that supports epigenetics is DNA methylation. DNA methylation is chemically stable, and such information is transmitted through cell division without changing the DNA sequence. Because of such characteristics, DNA methylation is considered to play a key role in various phenomena, such as tissue-specific gene expression, imprinting, X chromosome inactivation, and carcinogenesis. In recent years, many congenital or acquired diseases resulting from abnormality of the DNA methyltransferase gene or DNA methylation status, abnormality of DNA methylation in cloned animals, and the like have already been identified.

There have heretofore been a variety of methods aimed at analysis of DNA methylation. A variety of methods for analyzing DNA methylation have distinctive characteristics in terms of, for example, analysis sensitivity, completeness, resolution, and quantitative performance, and an adequate method is selected in accordance with the intended purpose. When the transcriptional repression mechanism of a specific gene is to be identified, for example, resolution at the single nucleotide level is necessary. When methylation frequency is to be analyzed, it is necessary to take quantitative performance and accuracy into consideration.

When detecting methylated DNA in a specific region, a nucleotide substitution reaction is carried out via bisulfite treatment to determine the DNA sequence. According to the nucleotide substitution reaction, unmethylated cytosine reacts with sodium bisulfite and it is converted into uracil. Since methylated cytosine does not react with sodium bisulfite, the methylation states of all cytosines can be detected as nucleotide differences in principle. Examples of conventional detection methods include a methylation-specific PCR (MSP) method of performing PCR, a real-time MSP method of performing quantitative PCR, bisulfite sequencing of performing TA cloning, the MassARRAY method of performing mass analysis, and pyrosequencing using a next-generation sequencer. In addition, the ICON-prove method, which does not require the bisulfite reaction, has been developed.

It is difficult to determine the expression levels of target proteins or microRNA based only on individual CpG methylation levels. Methylation patterns or continuity in such specific regions are important. While a variety of methods for detecting CpG methylation levels have been developed, methods for detecting CpG methylation patterns or continuity are limited to the bisulfite sequencing method.

The bisulfite-DGGE method was developed by P. Guldberg et al. (Non-Patent Document 2) based on the denaturing gradient gel electrophoresis (DGGE) method proposed by Abrams and Stanton (Non-Patent Document 1). According to the bisulfite-DGGE method, the sample after bisulfite treatment is amplified via PCR, and the amplicons thereof are then subjected to electrophoresis using a gel consisting of polyacrylamide and a denaturing agent having density gradient. Separation is carried out based on differences in the double-stranded DNA molecular weights in a polyacrylamide-density-gradient-dependent manner, separation is further carried out based on differences in the degrees of double-stranded DNA denaturation in a denaturing-density gradient-dependent manner, and separation based on differences between uracil (unmethylated cytosine) and cytosine (methylated cytosine) in the target region is then carried out. According to such method, visual evaluation can be performed, as with the case of the MSP method, and a band of a gel after electrophoresis can be used for sequencing. Compared with the bisulfite sequencing method, the bisulfite-DGGE method can be completed within a remarkably short period of time.

According to the bisulfite-DGGE method, however, PCR amplification is carried out after bisulfite treatment. This causes conversion of unmethylated cytosine into thymine, the resulting thymine is mixed with thymine that is originally present in the DNA sequence, and similar sequences then increase. Such increase often results in misannealing in PCR. When the number of PCR cycles is increased, accordingly, non-specific amplicons are disadvantageously amplified. When trace amounts of samples are to be analyzed or minor DNA methylation patterns are to be detected, it is necessary to increase the number of PCR cycles, and the resolution consequently deteriorates according to the bisulfite-DGGE method. Also, the bisulfite-DGGE method requires density gradients of both polyacrylamide and a denaturing agent, when preparing an electrophoresis gel. When the target is changed, accordingly, gel optimization becomes necessary, and such necessity disadvantageously complicates the procedure.

PRIOR ART DOCUMENTS

Non-Patent Documents

Non-Patent Document 1: Abrams, E. S. and Stanton, V. P. Jr., Use of denaturing gradient gel electrophoresis to study conformational transitions in nucleic acids, "Methods Enzymol.," 1992, Vol. 212, pp. 71-104

Non-Patent Document 2: Guldberg, P., Gronbak, K., Aggerholm, A., Platz, A., thor Straten, P., Ahrenkiel, V., Hokland, P., and Zeuthen, J., Detection of mutations in GC-rich DNA by bisulphite denaturing gradient gel electrophoresis, "Nucleic Acids Res.," 1998, Vol. 26, No. 6, pp. 1548-1549

SUMMARY OF THE INVENTION

Under the above-described circumstances, it is an object of the present invention to provide a method for efficiently detecting DNA methylation.

The present inventors have conducted concentrated studies in order to attain the above object. As a result, they have found that DNA methylation in a target region can be efficiently detected by treating DNA with bisulfite (hereafter, it may be occasionally referred to as "bisulfite treatment"), subjecting the DNA after bisulfite treatment to a first PCR and then to nested PCR, and subjecting the amplified DNA (amplicon) to denaturing gradient gel electrophoresis (hereafter, it may be occasionally referred to as "DGGE"). This has led to the completion of the present invention.

The present invention includes the following.

(1) A method for detecting DNA methylation comprising steps of:

subjecting DNA to bisulfite treatment;

subjecting the DNA after bisulfite treatment to a first PCR using the first set of primers corresponding to outer regions of the target region;

subjecting the amplified DNA after the first PCR to a second PCR using the second set of primers corresponding to the target region; and subjecting the amplified DNA after the second PCR to denaturing gradient gel electrophoresis, wherein the annealing positions of the second set of primers are located inside the annealing positions of the first set of primers relative to the target region.

(2) The method according to (1), wherein one of a pair of the second set of primers has a GC-clamp sequence at its 5' side.

(3) The method according to (1), wherein the density gradient of the denaturing gradient gel is limited to a denaturing density gradient.

This description includes part or all of the content as disclosed in the description and/or drawings of Japanese Patent Application No. 2010-098163, which is a priority document of the present application.

BRIEF DESCRIPTION OF THE DRAWINGS

FIG. 1 shows a sequence of a methylated region associated with human mucin core protein 1 (MUC1) gene promoter expression (SEQ ID NO: 2; the DNA sequence after bisulfite treatment, and uracil converted from unmethylated cytosine is indicated as "thymine").

FIG. 2 shows the results of analyzing methylation of a methylated region associated with MUC1 gene promoter expression by the method of the present invention.

FIG. 3 shows a sequence of a methylated region associated with human mucin core protein 2 (MUC2) gene promoter expression (SEQ ID NO: 7; the DNA sequence after bisulfite treatment, and uracil converted from unmethylated cytosine is indicated as "thymine").

FIG. 4 shows the results of analyzing methylation of a methylated region associated with MUC2 gene promoter expression by the method of the present invention.

FIG. 5 shows a sequence of a methylated region associated with human mucin core protein 4 (MUC4) gene promoter expression (SEQ ID NO: 12; the DNA sequence after bisulfite treatment, and uracil converted from unmethylated cytosine is indicated as "thymine").

FIG. 13 shows a comparison of the results of methylation analysis of a methylated region associated with human MUC4 gene promoter expression in human tissue samples obtained via surgery by the method of the present invention and expression analysis of a protein encoded by such gene via immunohistochemical staining.

FIG. 18 shows a sequence of a methylated region associated with human mucin core protein 5AC (MUC5AC) gene promoter expression (SEQ ID NO: 29; the DNA sequence after bisulfite treatment, and uracil converted from unmethylated cytosine is indicated as "thymine").

FIG. 19 shows the results of analyzing methylation of a methylated region associated with MUC5AC gene promoter expression by the method of the present invention.

FIG. 22 shows the results of a comparison of the detection performance of the bisulfite-DGGE method and that of the method of the present invention in tissue samples.

EMBODIMENTS FOR CARRYING OUT THE INVENTION

Figure 6:
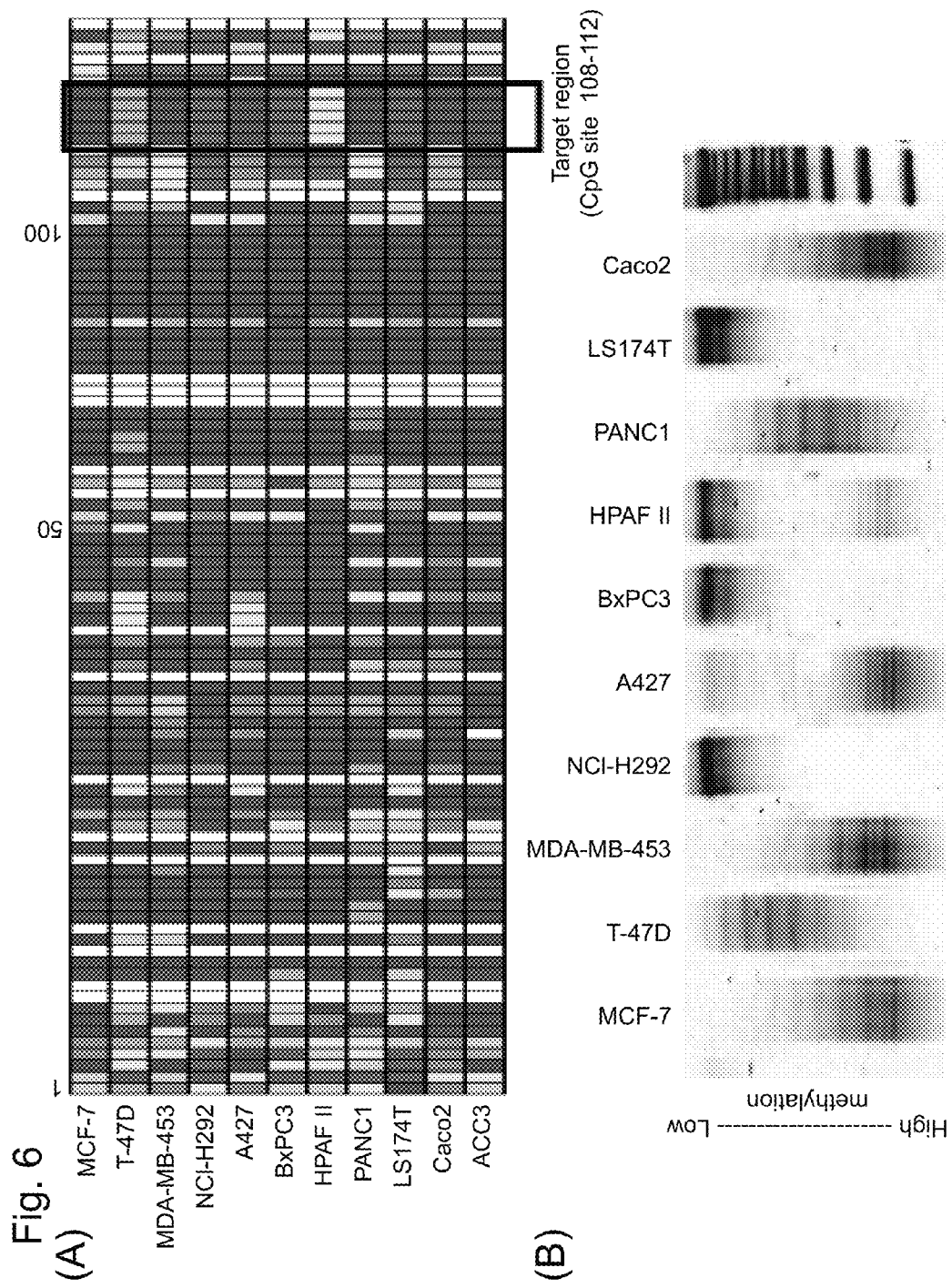
FIG. 6 shows the results of analyzing methylation of a methylated region associated with MUC4 gene promoter expression by the method of the present invention.

Hereafter, the present invention is described in detail.

The method for detecting DNA methylation of the present invention (hereafter, it is referred to as the "methylation-specific electrophoresis (MSE) method") comprises: (1) a step of subjecting DNA to bisulfite treatment; (2) a step of subjecting the DNA after bisulfite treatment to a first PCR using the first set of primers corresponding to outer regions of the target region; (3) a step of subjecting the amplified DNA after the first PCR to a second PCR using the second set of primers corresponding to the target region; and (4) a step of subjecting the amplified DNA after the second PCR to denaturing gradient gel electrophoresis. According to the MSE method, for example, DNA methylation in trace amounts of DNA samples can be detected, and DNA methylation patterns or continuity can be efficiently detected.

DNA that is applied to the MSE method may be derived (or extracted) from a biological sample (e.g., an organ, tissue, cell, or body fluid) originating from any organism (e.g., bacteria or mammalians such as humans) in which DNA methylation takes place. For example, DNA extracted from cancer-tissue-derived tissue, body fluid, or cells can be applied to the MSE method.

Hereafter, each step of the MSE method is described.

(1) Step of Subjecting DNA to Bisulfite Treatment

According to the MSE method, DNA is first subjected to bisulfite treatment. Thus, unmethylated cytosine is sulfonated by bisulfite, further deaminated via hydrolysis, and then converted into uracil via desulfonation in the presence of alkali. In contrast, methylated cytosine is not converted into uracil via bisulfite treatment. Thus, whether or not cytosine in the nucleotide sequence of CpG-containing DNA is methylated is determined based on conversion of cytosine into uracil via bisulfite treatment. DNA can be subjected to bisulfite treatment using a commercially available kit for bisulfite treatment (e.g., EpiTect Bisulfite Kits, Qiagen) in accordance with the instructions thereof.

(2) Step of Subjecting DNA After Bisulfite Treatment to First PCR

According to the MSE method, the DNA after bisulfite treatment is then subjected to a first PCR using the first set of primers corresponding to outer regions of the target region. Unmethylated cytosine is converted into thymine via PCR amplification following the bisulfite treatment, the resulting thymine is mixed with thymine that is originally present in the DNA sequence, and similar sequences thus increase. Such increase leads to misannealing in PCR. When the number of PCR cycles is increased, accordingly, non-specific amplicons are disadvantageously amplified. According to the MSE method, a first PCR is carried out using the first set of primers corresponding to outer regions of the target region in order to prevent the occurrence of such noise, and a second PCR (nested PCR) is then carried out in order to decrease such noise. Thus, the number of PCR cycles can be increased, and the detection limit can be enhanced (i.e., trace amounts of DNA samples can be used).

The term "target region" used herein refers to a region having a methylated state to be detected in DNA. An example of a target region is a CpG island (or a CpG site), which is a region in which CG dinucleotides are concentrated and to be methylated. For example, the presence of CpG islands in 5' upstream regions of many genes of mammalians is known. Also, the CpG site in DNA may be determined in advance by the MassARRAY method, and a region selectively comprising an important CpG site can be designated as a target region. According to such method of determining the target regions, the detection resolution can be enhanced. The length of the target region is, for example, 200 to 400 nucleotides.

A pair of primers of the first set of primers are designed to correspond to outer regions of the target region and anneal to such outer regions. Such outer regions can be located, for example, 10 to 100 nucleotides (preferably 20 to 80 nucleotides) away from each end of the target region in outward directions. The first set of primers can be composed of, for example, 15 to 30 nucleotides, and preferably 18 to 22 nucleotides.

PCR can be carried out by, for example, taking the length of the amplification product or GC content into consideration and adequately determining the composition of a PCR reaction solution (e.g., PCR buffer, polymerase dNTP mix, or primers), the temperature conditions, and the number of cycles for thermal denaturation, annealing, and extension. Such PCR conditions can be adequately determined (e.g., optimal conditions for polymerase to be used). Uracil converted from unmethylated cytosine is converted into thymine via such PCR.

(3) Step of Subjecting Amplified DNA After First PCR to Second PCR

According to the MSE method, the amplified DNA after the first PCR (the amplification product) is subjected to a second PCR using the second set of primers corresponding to the target region. The second PCR is also referred to as "nested PCR." Specifically, the second set of primers are designed inside the amplification product after the first PCR, and a second PCR is carried out using the amplification product after the first PCR as a new template.

The second set of primers are designed in such a manner that the annealing positions thereof are located inside the annealing positions of the first set of primers relative to the target region. Specifically, the annealing positions of the second set of primers are located at both ends of the target region or regions adjacent thereto. The second set of primers may partially overlap with the first set of primers, provided that the annealing positions of the second set of primers are located inside the annealing positions of the first set of primers. The second set of primers can be composed of, for example, 15 to 30 nucleotides, and preferably 18 to 22 nucleotides. By adding the GC-clamp sequence to the 5' side of one of a pair of the second set of primers (e.g., a forward (sense) primer), the separability can be improved in the subsequent step of denaturing gradient gel electrophoresis. The term "GC-clamp sequence" used herein refers to a G-C-rich stable sequence comprising about 30 to 50 nucleotides. An example thereof is the nucleotide sequence as shown in SEQ ID NO: 1.

As with the case of the first PCR, PCR can be carried out by, for example, taking the length of the target region or GC content into consideration and adequately determining the composition of a PCR reaction solution (e.g., PCR buffer, polymerase dNTP mix, or primers), and the temperature conditions and the number of cycles for thermal denaturation, annealing, and extension.

(4) Step of Subjecting Amplified DNA After Second PCR to Denaturing Gradient Gel Electrophoresis According to the MSE method, the amplified DNA after the second PCR is subjected to denaturing gradient gel electrophoresis to separate the amplified DNA, and methylation patterns or continuity can be visually evaluated.

In the case of the conventional bisulfite-DGGE method, samples contained many non-specific amplified fragments. In order to enhance the efficiency for separation based on DNA chain length, accordingly, density gradients of both a gel component (i.e., acrylamide) and a denaturing agent were necessary when preparing an electrophoresis gel. Thus, the conventional bisulfite-DGGE method required two types of density gradients, and gel optimization procedures for each target region were laborious. In contrast, the MSE method performs the first PCR and the second PCR (i.e., nested PCR) so as to suppress non-specific amplification, thereby reducing noise caused by non-specific amplified fragments. With the use of amplified DNA with high detection sensitivity, accordingly, a gel with the density gradient of a denaturing agent alone can be used for the MSE method, reproducibility can be enhanced, and gel optimization can be easily performed.

A denaturing gradient gel is prepared using, for example, a gel component (acrylamide), a denaturing agent such as a combination of urea and formamide, and TAE buffer. When a polyacrylamide gel is used and a combination of urea and formamide is used as a denaturing agent, specifically, a gel is prepared so as to bring the acrylamide density to, for example, 6% to 15% (preferably 8% to 10%) therein, and have the density gradient of the combination of urea and formamide of 10%→50% to 20%→30% (the density gradient interval is preferably 10% or higher) in accordance with the length of the amplification product. Optimization conditions are examined with reference to a gel with a broad density gradient interval (10% to 50%), and a method for narrowing the density gradient interval is examined. When the detected band exhibits a smear, acrylamide density is increased. The gradient of a denaturing agent in a gel is adjusted to increase in the direction from the cathode to the anode of electrophoresis (i.e., the direction of DNA migration).

According to the MSE method, the amplified DNA after the second PCR (e.g., 4 to 15 µl, preferably 5 to 10 µl) is applied to a denaturing gradient gel and then subjected to electrophoresis. For example, electrophoresis is carried out in an electrophoresis bath at 60° C. at a constant voltage of 70 to 250 V for 300 to 900 minutes.

After electrophoresis, a denaturing gradient gel can be stained with ethidium bromide or GelRed, so that the band of the amplified DNA applied can be visually observed. The GC pair is bound by three hydrogen bonds, and the AT pair is bound by two hydrogen bonds. Thus, a GC bond is more tolerant to a denaturing agent than an AT bond. That is, the migration level of DNA having many GC bonds in a denaturing gradient gel is higher than that of DNA having many AT bonds.

According to the MSE method, unmethylated cytosine in DNA is converted into uracil and then into thymine. Thus, the velocity of migration of amplified DNA corresponding to the target region having unmethylated cytosine is slower than that of amplified DNA corresponding to the target region having methylated cytosine, and DNA of the former type would be located at a position closer to the cathode of the denaturing gradient gel. In contrast, the velocity of migration of amplified DNA corresponding to the target region having methylated cytosine is high, and such DNA would be located at a position closer to the anode of the denaturing gradient gel. Accordingly, the target region having methylated cytosine can be distinguished from the target region having unmethylated cytosine based on such differences in migration behavior, and methylation patterns or continuity in the target region can be evaluated.

In addition, the target band may be cleaved from the electrophoresed denaturing gradient gel, amplified DNA in the band may be extracted, and the nucleotide sequence of the amplified DNA extracted may be determined. Thus, the DNA methylation status can be evaluated at a single-nucleotide level.

According to the MSE method described above, DNA methylation can be efficiently and easily detected. DNA methylation is known to play a key role in various phenomena, such as tissue-specific gene expression, imprinting, X chromosome inactivation, and carcinogenesis. Congenital or acquired diseases resulting from abnormalities of the DNA methyltransferase gene or the DNA methylation status and abnormalities of DNA methylation in cloned animals have been known. Thus, the MSE method can be effectively used for diagnosis of diseases or the like associated with DNA methylation.

Also, the MSE method is advantageous over conventional methods for detecting DNA methylation as described below.

The MSP method that has heretofore often been employed in the field of epigenetics is capable of visual evaluation of DNA methylation. According to the MSP method, methylation is detected based on a CpG site at which a primer is designed. When methylation patterns are uniform at the CpG site in the target region, accordingly, evaluation can be made with high resolution. When methylation patterns are mosaic-like, however, the resolution of the methylation analysis would deteriorate. Also, detection of methylation in the real-time MSP method depends on a CpG site at which a prove is designed, and, accordingly, a target region that can be evaluated is small. As with the case of the MSP method, the resolution would deteriorate when methylation patterns at the CpG site in the target region are mosaic-like. According to the MSE method, however, all methylation patterns at the CpG site of the amplified target region can be visually evaluated.

According to bisulfite sequencing, the sequence of the amplified target region is determined via TA cloning. Such method, however, necessitates the use of 10 or more clones in order to attain the "probability" and thus is time-consuming. While a majority of methylation patterns can be evaluated in a cost-effective manner, such method is not suitable for evaluation of a minority of methylation patterns. By increasing the number of PCR amplifications (i.e., the number of cycles), minor methylation patterns can be evaluated by the MSE method. In addition, an individual band may be cleaved after electrophoresis and purified, and the sequence of the target region in the band may then be determined. Thus, the sequences can be inspected regarding methylation patterns, and all sequences can be subjected to evaluation equivalent to that according to bisulfite sequencing.

Further, the MassARRAY method is excellent in terms of both quantitative properties and resolution, allowing evaluation of methylation of each CpG. However, CpG methylation patterns cannot be determined. When the target region is contaminated with CpG methylation patterns, accordingly, evaluation by the MassARRAY method is difficult. In contrast, the MSE method can yield detection sensitivity equivalent to that attained by the MassARRAY method, and methylation patterns can be evaluated.

Hereafter, the present invention is described in greater detail with reference to the Examples, although the technical scope of the present invention is not limited thereto.

Example 1

Methylation Analysis of Methylated Region Associated with Mucin Core Protein 1 (MUC1) Gene Promoter Expression via MSE In Example 1, methylation of a methylated region associated with human MUC1 gene promoter expression was analyzed by the MSE method. FIG. 1 shows a sequence of a methylated region associated with human MUC1 gene promoter expression (SEQ ID NO: 2; the DNA sequence after bisulfite treatment, and uracil converted from unmethylated cytosine is indicated as "thymine"). The region comprises the CpG sites 172-181. In Example 1, a region comprising these CpG sites is designated as a target region. As in the case of the literature (Norishige Yamada, Yukari Nishida, Hideaki Tsutsumida, Tomofumi Hamada, Masamichi Goto, Michiyo Higashi, Mitsuharu Nomoto, and Suguru Yonezawa, 2008, MUC1 expression is regulated by DNA methylation and histone H3-K9 modification in cancer cells, Cancer Res., 68 (8): 2708-16), the CpG site was numbered successively from an upstream region of a putative promoter region of the human MUC1 gene (2,753 bp upstream from the origin of transcription in the gene).

1-1. Sample Preparation and Method

DNA samples were extracted from the following cell strains using the DNeasy Blood & Tissue Kit (Qiagen); HPAF II (human pancreatic cancer), BxPC3 (human pancreatic cancer), PANC1 (human pancreatic cancer), MCF-7 (human breast cancer), T-47D (human breast cancer), MDA-MB-453 (human breast cancer), Caco2 (human colon adenocarcinoma), LS174T (human large bowel cancer), A427 (human lung cancer), and NCI-H292 (human lung cancer).

Subsequently, the extracted DNA samples were subjected to bisulfite treatment using EpiTect Bisulfite Kits (Qiagen).

The DNA samples after bisulfite treatment were subjected to PCR performed with the use of the primers shown below. Set of primers (the nucleotide sequence indicated by lowercase letters is the GC clamp):

```
Primer 1-1:
                                        (SEQ ID NO: 3)
5'-AAAGGGGGAGGTTAGTTGGA-3';

Primer 1-2:
                                        (SEQ ID NO: 4)
5'-AAACAACCCACTCCCCACCT-3';

Primer 1-3:
                                        (SEQ ID NO: 5)
5'-cgcccgccgcgcgcggcggcggggcggggcggggcacggggggAAGAGGTAGGAGGTAGGGGA-3';
and Primer 1-4:
                                        (SEQ ID NO: 6)
5'-AAAACAAAACAAATTCAAAC-3'
```

As shown in FIG. 1, the $1^{st}$ PCR was carried out with the use of Primer 1-1 and Primer 1-2, and the $2^{nd}$ PCR (nested PCR) was carried out with the use of Primer 1-3 and Primer 1-4. The AmpliTaq Gold® Fast PCR Master Mix (Applied Biosystem) was used as polymerase. PCR conditions and temperature conditions are shown in Table 1.

TABLE 1

| Composition of reaction solution for $1^{st}$ PCR | |
|---|---|
| DNA after bisulfite treatment | 1 μl |
| Master Mix | 10 μl |
| Primer 1-1 | 0.3 μl |
| Primer 1-2 | 0.3 μl |
| dH₂O | 8.4 μl |
| Total | 20 μl |

| $1^{st}$ PCR temperature conditions | | |
|---|---|---|
| 95° C. | 10 min | |
| 96° C. | 5 sec | |
| 63° C. | 5 sec | 40 cycles |
| 68° C. | 9 sec | |
| 72° C. | 10 sec | |

| Composition of reaction solution for $2^{nd}$ PCR | |
|---|---|
| $1^{st}$ PCR amplicon | 2 μl |
| Master Mix | 10 μl |
| Primer 1-3 | 0.3 μl |
| Primer 1-4 | 0.3 μl |
| dH₂O | 7.4 μl |
| Total | 20 μl |

| $2^{nd}$ PCR temperature conditions | | |
|---|---|---|
| 95° C. | 10 min | |
| 96° C. | 5 sec | |
| 53° C. | 5 sec | 45 cycles |
| 68° C. | 9 sec | |
| 72° C. | 10 sec | |

Subsequently, the reaction solution after the $2^{nd}$ PCR was subjected to DGGE using a denaturing gradient gel having the conditions for DGGE gel shown in Table 2. Electrophoresis was carried out in an electrophoresis bath at 60° C. at a constant voltage of 230 V for 300 minutes. The Dcode System (BIO-RAD) was used as an electrophoresis bath.

TABLE 2

Conditions for DGGE gel

10% acrylamide gel
Denaturing density gradient: 30% to 40%

Composition of 30% denaturing gel

| | |
|---|---|
| 40% stock solution | 3.0 ml |
| 50x TAE buffer | 0.3 ml |
| Urea | 1.88 g |
| Formamide | 1.8 ml |

Composition of 40% denaturing gel

| | |
|---|---|
| 40% stock solution | 3.0 ml |
| 50x TAE buffer | 0.3 ml |
| Urea | 2.51 g |
| Formamide | 2.4 ml |

40% stock solution: Bio-Rad, 40 (w/v)% acrylamide/bis mixed solution (37.5:1);
50x TAE buffer: Nacalai Tesque, Tris-acetate-EDTA buffer (50x);
Urea: Nacalai Tesque, SP grade;
Formamide: Nacalai Tesque, SP grade 1-2. Results of Analysis FIG. 2 shows the results of analysis of the cell strains. Panel (A) shows the results of evaluation of methylation in a methylated region associated with human MUC1 gene promoter expression of the cell strains by the MassARRAY method. The MassARRAY method was performed with reference to the literature (Norishige Yamada, Yukari Nishida, Hideaki Tsutsumida, Tomofumi Hamada, Masamichi Goto, Michiyo Higashi, Mitsuharu Nomoto, and Suguru Yonezawa, 2008, MUC1 expression is regulated by DNA methylation and histone H3-K9 modification in cancer cells, Cancer Res., 68(8): 2708-16). The color gradient from green to yellow to red indicates the degree of methylation from unmethylation (0%) to methylation (100%). A region framed by a rectangle is the target region of Example 1 (i.e., the CpG sites). Panel (B) shows a photograph of a gel after DGGE conducted in Example 1. The gradient of a denaturing agent in a gel is adjusted to increase in the direction from the cathode to the anode of electrophoresis (from the top toward the bottom in the panel).

As shown in FIG. 2, the results of evaluation of methylation by the MSE method were highly correlated with those of evaluation by the MassARRAY method. While the A427 strain and the NCI-H292 strain were not evaluated by the MassARRAY method, the methylation levels thereof were easily deduced to be equivalent to those of the MDA-MB-453 strain and the Caco2 strain.

Example 2

Methylation Analysis of Methylated Region Associated with Mucin Core Protein 2 (MUC2) Gene Promoter Expression via MSE In Example 2, methylation of a methylated region associated with human MUC2 gene promoter expression was analyzed by the MSE method. FIG. 3 shows a sequence of a methylated region associated with human MUC2 gene promoter expression (SEQ ID NO: 7; the DNA sequence after bisulfite treatment, and uracil converted from unmethylated cytosine is indicated as "thymine"). The region comprises the CpG sites 36-43. In Example 2, a region comprising these CpG sites is designated as a target region. As in the case of the literature (Norishige Yamada, Tomofumi Hamada, Masamichi Goto, Hideaki Tsutsumida, Michiyo Higashi, Mitsuharu Nomoto, and Suguru Yonezawa, 2006, MUC2 expression is regulated by histone H3 modification and DNA methylation in pancreatic cancer, Int. J. Cancer, 119 (8): 1850-7), the CpG site was numbered successively from an upstream region of a putative promoter region of the human MUC2 gene (1,989 bp upstream from the origin of transcription in the gene).

2-1. Sample Preparation and Method

In the same manner as in Example 1, DNA samples were extracted from the following cell strains using the DNeasy Blood & Tissue Kit (Qiagen); HPAF II, BxPC3, PANC1, MCF-7, T-47D, MDA-MB-453, Caco2, LS174T, A427, NCI-H292, and ACC3 (adenoid cystic carcinoma), and the extracted DNA samples were subjected to bisulfite treatment using EpiTect Bisulfite Kits (Qiagen).

The DNA samples after bisulfite treatment were subjected to PCR performed with the use of the primers shown below. Set of primers (the nucleotide sequence indicated by lowercase letters is the GC clamp):

```
Primer 2-1:
                                                  (SEQ ID NO: 8)
5'-TTTGGGGTTAGGTTTGGAAG-3';

Primer 2-2:
                                                  (SEQ ID NO: 9)
5'-ACCTTCTTCAAAATAAAACAACC-3';

Primer 2-3:
                                                  (SEQ ID NO: 10)
5'-cgcccgccgcgcgcggcgggcggggcggggcacggggggTTTTAGAGTTTGGGTTTTAG-3';
and Primer 2-4:
                                                  (SEQ ID NO: 11)
5'-TAACCTAAATACCAACACACA-3'
```

As shown in FIG. 3, the 1$^{st}$ PCR was carried out with the use of Primer 2-1 and Primer 2-2, and the 2$^{nd}$ PCR (nested PCR) was carried out with the use of Primer 2-3 and Primer 2-4. The AmpliTaq Gold® Fast PCR Master Mix (Applied Biosystem) was used as polymerase. PCR conditions and temperature conditions are shown in Table 3.

TABLE 3

Composition of reaction solution for 1$^{st}$ PCR

| | |
|---|---|
| DNA after bisulfite treatment | 1 μl |
| Master Mix | 10 μl |
| Primer 2-1 | 0.3 μl |
| Primer 2-2 | 0.3 μl |
| dH$_2$O | 8.4 μl |
| Total | 20 μl |

TABLE 3-continued

1st PCR temperature conditions

| | | |
|---|---|---|
| 95° C. | 10 min | |
| 96° C. | 5 sec | |
| 59° C. | 5 sec | } 40 cycles |
| 68° C. | 9 sec | |
| 72° C. | 10 sec | |

Composition of reaction solution for 2nd PCR

| | |
|---|---|
| 1st PCR amplicon | 2 μl |
| Master Mix | 10 μl |
| Primer 2-3 | 0.3 μl |
| Primer 2-4 | 0.3 μl |
| dH₂O | 7.4 μl |
| Total | 20 μl |

2nd PCR temperature conditions

| | | |
|---|---|---|
| 95° C. | 10 min | |
| 96° C. | 5 sec | |
| 51° C. | 5 sec | } 45 cycles |
| 68° C. | 9 sec | |
| 72° C. | 10 sec | |

Subsequently, the reaction solution after the 2nd PCR was subjected to DGGE using a denaturing gradient gel having the conditions for DGGE gel shown in Table 4. The electrophoresis conditions and the electrophoresis bath employed in Example 1 were also employed herein.

TABLE 4

Conditions for DGGE gel

10% acrylamide gel
Denaturing density gradient: 20% to 28%

Composition of 20% denaturing gel

| | |
|---|---|
| 40% stock solution | 3.0 ml |
| 50x TAE buffer | 0.3 ml |
| Urea | 1.25 g |
| Formamide | 1.2 ml |

Composition of 28% denaturing gel

| | |
|---|---|
| 40% stock solution | 3.0 ml |
| 50x TAE buffer | 0.3 ml |
| Urea | 1.76 g |
| Formamide | 1.7 ml |

40% stock solution: Bio-Rad, 40 (w/v)% acrylamide/bis mixed solution (37.5:1);
50x TAE buffer: Nacalai Tesque, Tris-acetate-EDTA buffer (50x);
Urea: Nacalai Tesque, SP grade;
Formamide: Nacalai Tesque, SP grade

2-2. Results of Analysis

FIG. 4 shows the results of analysis of the cell strains. Panel (A) shows the results of evaluation of methylation in a methylated region associated with human MUC2 gene promoter expression of the cell strains by the MassARRAY method. The MassARRAY method was performed with reference to the literature (Norishige Yamada, Tomofumi Hamada, Masamichi Goto, Hideaki Tsutsumida, Michiyo Higashi, Mitsuharu Nomoto, and Suguru Yonezawa, 2006, MUC2 expression is regulated by histone H3 modification and DNA methylation in pancreatic cancer, Int. J. Cancer, 119 (8): 1850-7). A region framed by a rectangle is the target region of Example 2 (i.e., the CpG sites). Panel (B) shows a photograph of a gel after DGGE conducted in Example 2. The gradient of a denaturing agent in a gel is adjusted to increase in the direction from the cathode to the anode of electrophoresis (from the top toward the bottom in the panel).

As shown in FIG. 4, the results of evaluation of methylation in the MUC2 promoter region by the MSE method were highly correlated with those of evaluation by the MassARRAY method.

Example 3

Methylation Analysis of Methylated Region Associated with Mucin Core Protein 4 (MUC4) Gene Promoter Expression via MSE In Example 3, methylation of a methylated region associated with human MUC4 gene promoter expression was analyzed by the MSE method. FIG. 5 shows a sequence of a methylated region associated with human MUC4 gene promoter expression (SEQ ID NO: 12; the DNA sequence after bisulfite treatment, and uracil converted from unmethylated cytosine is indicated as "thymine"). The region comprises the CpG sites 108-112. In Example 3, a region comprising these CpG sites is designated as a target region. As in the case of the literature (Norishige Yamada, Yukari Nishida, Hideaki Tsutsumida, Masamichi Goto, Michiyo Higashi, Mitsuharu Nomoto, and Suguru Yonezawa, 2009, Promoter CpG methylation in cancer cells contributes to regulation of MUC4, Br. J. Cancer, 100 (2): 344-51), the CpG site was numbered successively from an upstream region of a putative promoter region of the human MUC4 gene (3,622 bp upstream from the origin of transcription in the gene).

3-1. Sample Preparation and Method

In the same manner as in Example 1, DNA samples were extracted from the following cell strains using the DNeasy Blood & Tissue Kit (Qiagen); HPAF II, BxPC3, PANC1, MCF-7, T-47D, MDA-MB-453, Caco2, LS174T, A427, NCI-H292, and ACC3, and the extracted DNA samples were subjected to bisulfite treatment using EpiTect Bisulfite Kits (Qiagen).

The DNA samples after bisulfite treatment were subjected to PCR performed with the use of the primers shown below.
Set of primers (the nucleotide sequence indicated by lowercase letters is the GC clamp):

Primer 4-1:
(SEQ ID NO: 13)
5'-TAGTGGGGTGGGGTTGA-3';

Primer 4-2:
(SEQ ID NO: 14)
5'-AAACACCCAAAAAACCC-3';

Primer 4-3:
(SEQ ID NO: 15)
5'-cgcccgccgcgcgcggcgggcggggcggggcacgggggAGGAGAGAAAAGGGTGATTA-3';
and

```
Primer 4-4:
5'-ACCCAAAAAACCCTCCTCCA-3'
```
(SEQ ID NO: 16)

As shown in FIG. 5, the 1$^{st}$ PCR was carried out with the use of Primer 4-1 and Primer 4-2, and the 2$^{nd}$ PCR (nested PCR) was carried out with the use of Primer 4-3 and Primer 4-4. The AmpliTaq Gold® Fast PCR Master Mix (Applied Biosystem) was used as polymerase. PCR conditions and temperature conditions are shown in Table 5.

TABLE 5

| Composition of reaction solution for 1$^{st}$ PCR | |
| --- | --- |
| DNA after bisulfite treatment | 1 μl |
| Master Mix | 10 μl |
| Primer 4-1 | 0.3 μl |
| Primer 4-2 | 0.3 μl |
| dH$_2$O | 8.4 μl |
| Total | 20 μl |

| 1$^{st}$ PCR temperature conditions | | |
| --- | --- | --- |
| 95° C. | 10 min | |
| 96° C. | 5 sec | |
| 57° C. | 5 sec | 40 cycles |
| 68° C. | 9 sec | |
| 72° C. | 10 sec | |

| Composition of reaction solution for 2$^{nd}$ PCR | |
| --- | --- |
| 1$^{st}$ PCR amplicon | 2 μl |
| Master Mix | 10 μl |
| Primer 4-3 | 0.3 μl |
| Primer 4-4 | 0.3 μl |
| dH$_2$O | 7.4 μl |
| Total | 20 μl |

| 2$^{nd}$ PCR temperature conditions | | |
| --- | --- | --- |
| 95° C. | 10 min | |
| 96° C. | 5 sec | |
| 66° C. | 5 sec | 45 cycles |
| 68° C. | 9 sec | |
| 72° C. | 10 sec | |

Subsequently, the reaction solution after the 2$^{nd}$ PCR was subjected to DGGE using a denaturing gradient gel having the conditions for DGGE gel shown in Table 6. The electrophoresis conditions and the electrophoresis bath employed in Example 1 were also employed herein.

TABLE 6

| Conditions for DGGE gel |  |
| --- | --- |
| 10% acrylamide gel | |
| Denaturing density gradient: 25% to 45% | |
| Composition of 25% denaturing gel | |
| 40% stock solution | 3.0 ml |
| 50× TAE buffer | 0.3 ml |
| Urea | 1.57 g |
| Formamide | 1.5 ml |
| Composition of 45% denaturing gel | |
| 40% stock solution | 3.0 ml |
| 50× TAE buffer | 0.3 ml |
| Urea | 2.82 g |
| Formamide | 2.7 ml |

40% stock solution: Bio-Rad, 40 (w/v)% acrylamide/bis mixed solution (37.5:1);
50× TAE buffer: Nacalai Tesque, Tris-acetate-EDTA buffer (50×);
Urea: Nacalai Tesque, SP grade;
Formamide: Nacalai Tesque, SP grade 3-2. Results of Analysis FIG. 6 shows the results of analysis of the cell strains. Panel (A) shows the results of evaluation of methylation in a methylated region associated with human MUC4 gene promoter expression of the cell strains by the MassARRAY method. The MassARRAY method was performed with reference to the literature (Norishige Yamada, Yukari Nishida, Hideaki Tsutsumida, Masamichi Goto, Michiyo Higashi, Mitsuharu Nomoto, and Suguru Yonezawa, 2009, Promoter CpG methylation in cancer cells contributes to regulation of MUC4, Br. J. Cancer, 100 (2): 344-51). A region framed by a rectangle is the target region of Example 3 (i.e., the CpG sites). Panel (B) shows a photograph of a gel after DGGE conducted in Example 3. The gradient of a denaturing agent in a gel is adjusted to increase in the direction from the cathode to the anode of electrophoresis (from the top toward the bottom in the panel).

As shown in FIG. 6, the results of evaluation of methylation by the MSE method were highly correlated with those of evaluation by the MassARRAY method.

Example 4

Examination of Detection Limit of MSE

In order to examine the detection limit of the MSE method, as shown in the methylation analysis of a methylated region associated with human MUC1 gene promoter expression conducted in Example 1, the number of the cell strains exhibiting a high DNA methylation level (PANC 1) and that of the cell strains exhibiting a low DNA methylation level (BxPC3) were determined. DNAs were extracted from the cell mixtures prepared depending on proportions, DNAs subjected to bisulfate treatment were designated as DNA samples, and the detection limits of the bands thereof were inspected. The content of DNAs derived from the BxPC3 cell strains was successively reduced from 100% to 0.1%, and samples consisting of DNAs derived from the PANC 1 cell strains (i.e., the samples containing no DNAs derived from the BxPC3 cell strains) were prepared. PCR and DGGE were performed in the same manner as in Example 1.

Figure 7:
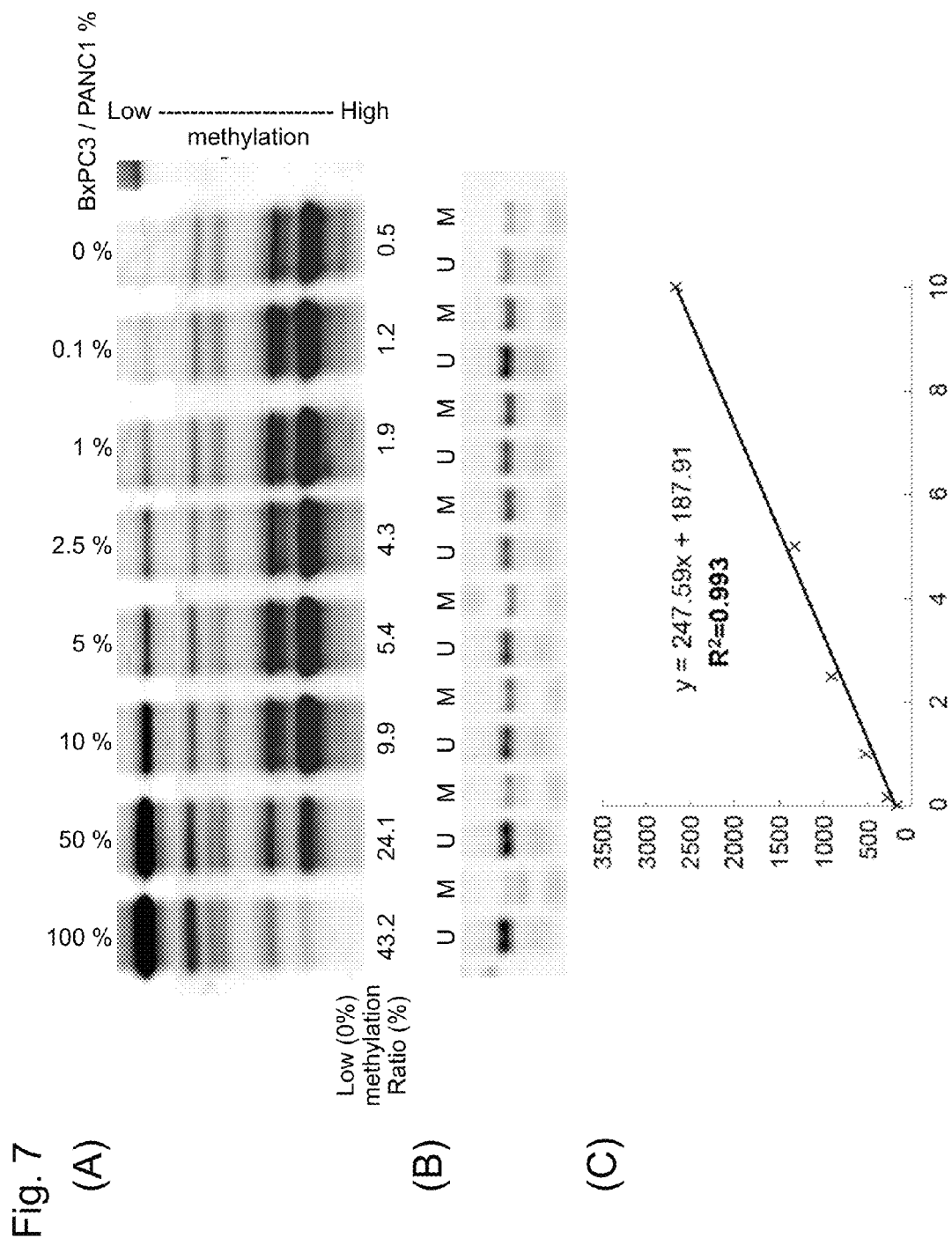
FIG. 7 shows the results of examining the detection limit of the method of the present invention.

The results are shown in FIG. 7. Panel (A) shows a photograph of a gel after DGGE conducted in Example 4. The gradient of a denaturing agent in a gel is adjusted to increase in the direction from the cathode to the anode of electrophoresis (from the top toward the bottom in the panel). Panel (B) shows the results of methylation analysis by the MSP method conducted with the use of the same samples. The MSP method was carried out with reference to the literature (Norishige Yamada, Yukari Nishida, Hideaki Tsutsumida, Tomofumi Hamada, Masamichi Goto, Michiyo Higashi, Mitsuharu Nomoto, and Suguru Yonezawa, 2008, MUC1 expression is regulated by DNA methylation and histone H3-K9 modification in cancer cells, Cancer Res., 68 (8): 2708-16) using the set of primers: MSP-UL (GGGGATTGGTATAAAGTGG-TAGGT: SEQ ID NO: 17); MSP-UR (AAAACAAAACAAT-TCAAACAAACA: SEQ ID NO: 18); MSP-ML (GATCGG-TATAAAGCGGTAGGC: SEQ ID NO: 19); and MSP-MR (AAAACAAAACAAATTCAAACAAACG: SEQ ID NO: 20).

In Panel (B), "U" indicates "unmethylation" and "M" indicates "methylation." Panel (C) shows a chart prepared by quantifying the emission from the unmethylated band in Example 4 with ImageJ and blotting the obtained data with reference to the DNA content derived from the BxPC3 cell strains. The horizontal axis represents a DNA content derived from the BxPC3 cell strains (%).

As shown in FIG. 7(A), the level of the unmethylated band lowers as the DNA content derived from the BxPC3 cell strains lowers. As shown in FIG. 7(B), the emission from the unmethylated band was quantified with ImageJ, the obtained data were blotted with reference to the DNA content derived from the BxPC3 cell strains, and $R^2$ of 0.993 was obtained (i.e., a very high correlation). The results demonstrate that the MSE method is capable of detection at a significant level even when a DNA content is 0.1% and the detection limit is lower than 0.1%. The detection limit attained by a conventional method for assaying methylation is 10% via the MassARRAY method, and it is 5% via pyrosequencing. This suggests that detection by the MSE method is performed with very high accuracy.

Example 5

Comparison of Results of Methylation Analysis of Methylated Region Associated with Human MUC1, MUC2, and MUC4 Gene Promoter Expression in Normal Mucosa and Cancer Tissue of the Human Large Bowel via MSE, Analysis of mRNA Expression of Such Genes, and Protein Expression Analysis via Immunohistochemical Staining Regarding normal mucosa and cancer tissue of the human large bowel, human colon samples prepared via crypt isolation that can be ideally separated without including stroma were subjected to the methylation analysis of a methylated region associated with human MUC1 (FIG. 8), MUC2 (FIG. 9), and MUC4 (FIG. 10) gene promoter expression by the MSE method in the same manner as in Examples 1 to 3. mRNA expression of such genes was analyzed, expression of proteins encoded by such genes was analyzed via immunohistochemical staining, and the results were compared.

Figure 8:
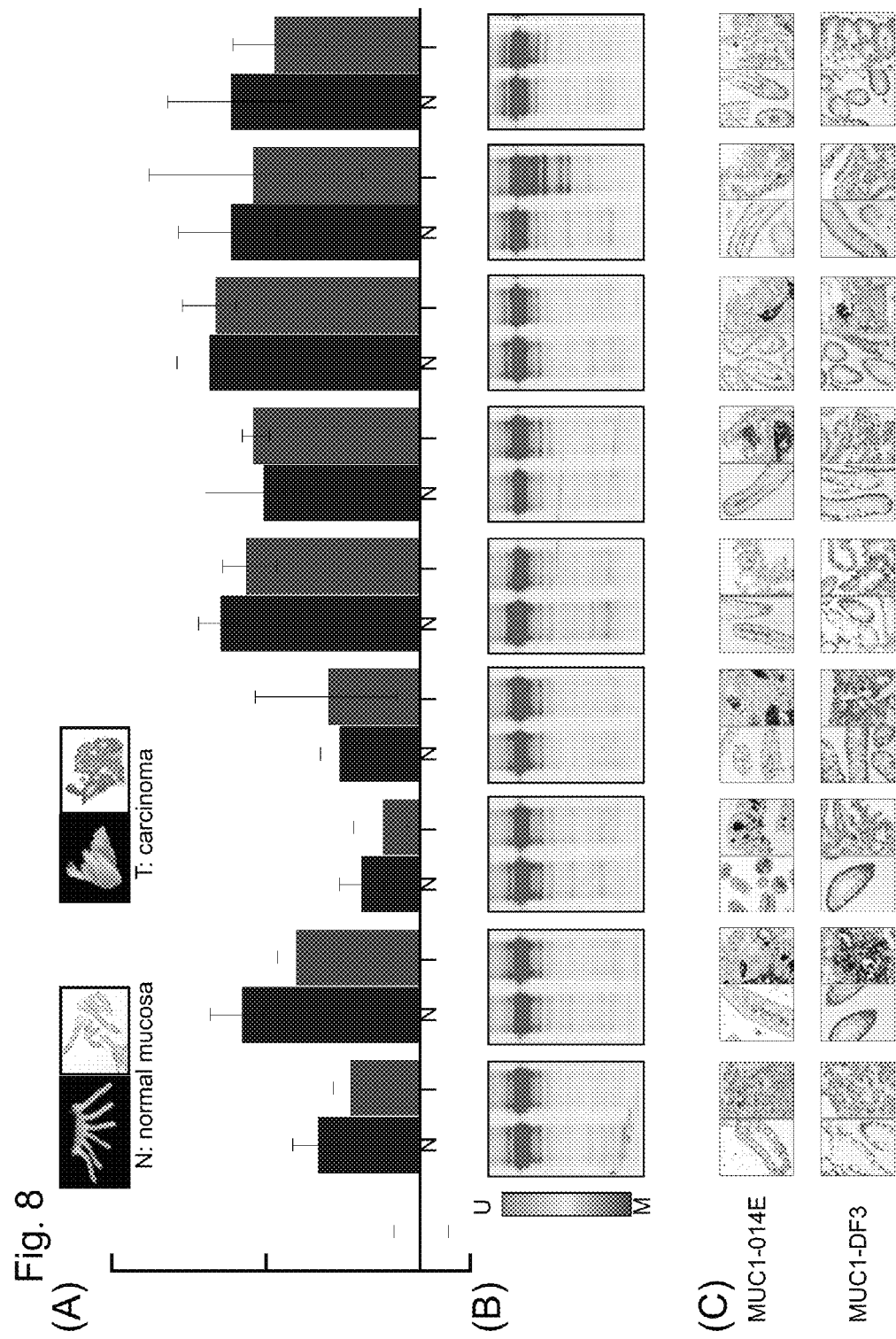
FIG. 8 shows a comparison of the results of methylation analysis of a methylated region associated with human MUC1 gene promoter expression in normal mucosa and cancer tissue of the human large bowel by the method of the present invention, analysis of mRNA expression of such gene, and protein expression analysis via immunohistochemical staining.
Figure 9:
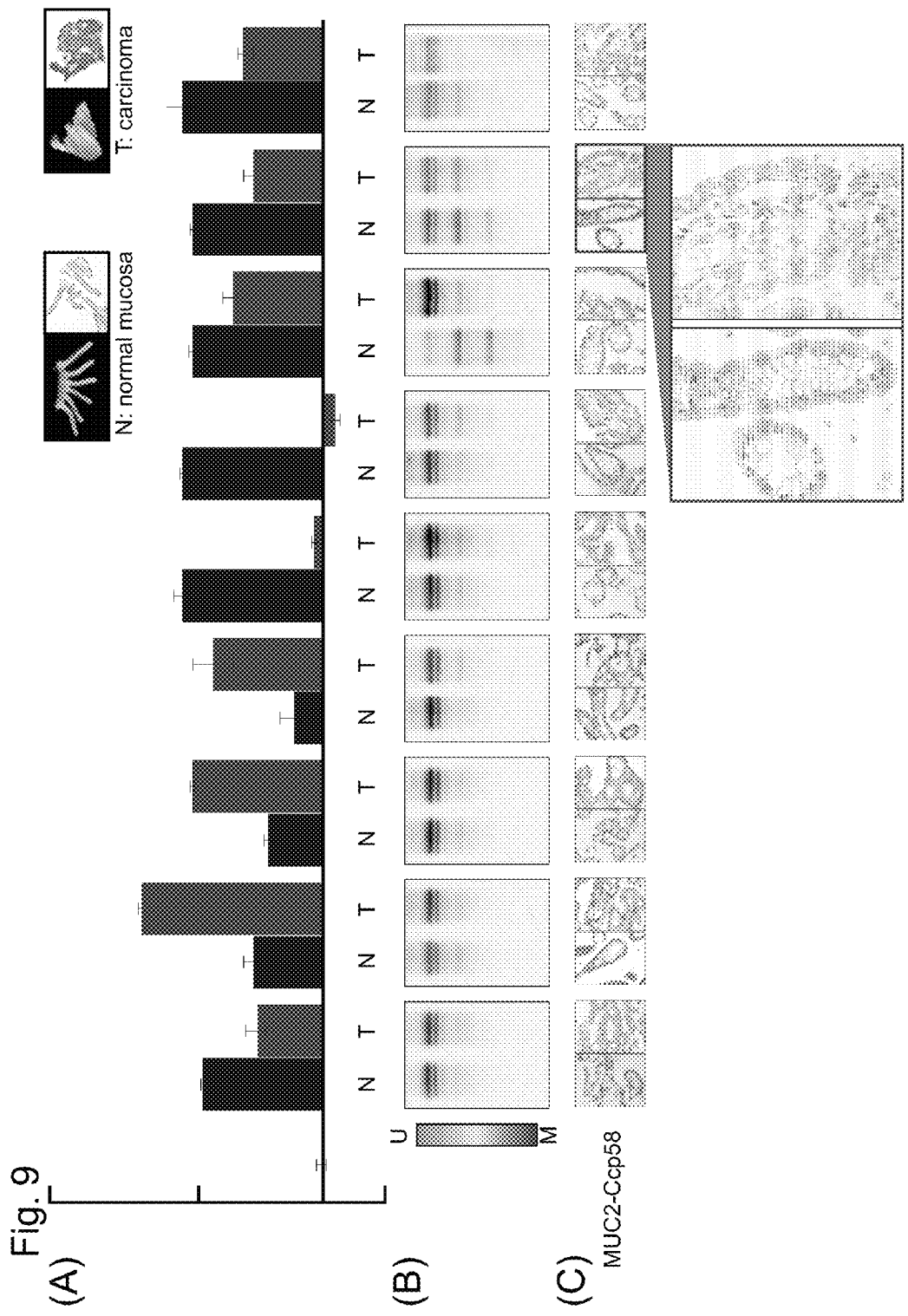
FIG. 9 shows a comparison of the results of methylation analysis of a methylated region associated with human MUC2 gene promoter expression in normal mucosa and cancer tissue of the human large bowel by the method of the present invention, analysis of mRNA expression of such gene, and protein expression analysis via immunohistochemical staining.
Figure 10:
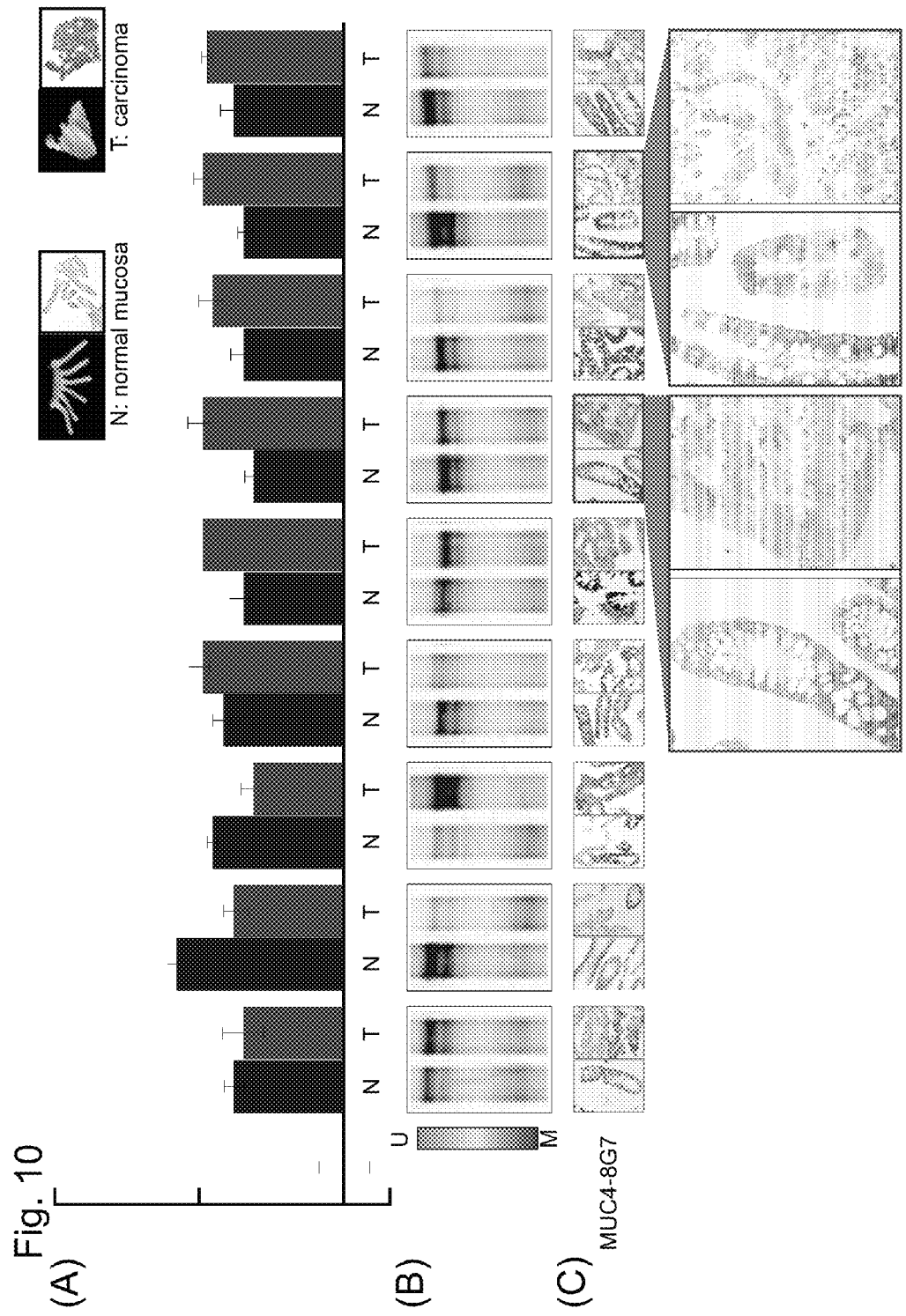
FIG. 10 shows a comparison of the results of methylation analysis of a methylated region associated with human MUC4 gene promoter expression in normal mucosa and cancer tissue of the human large bowel by the method of the present invention, analysis of mRNA expression of such gene, and protein expression analysis via immunohistochemical staining.

The results are shown in FIGS. 8 to 10. In FIGS. 8 to 10, "N" indicates a normal mucosa sample of the human large bowel, and "T" indicates a cancer tissue sample of the human large bowel. Panel (A) shows the mRNA expression levels in the samples detected by RT-PCR. Panel (B) shows a photograph of a gel after DGGE by the MSE method. The gradient of a denaturing agent in a gel is adjusted to increase in the direction from the cathode to the anode of electrophoresis (from the top toward the bottom in the panel). Accordingly, "U" indicates "unmethylation" and "M" indicates "methylation." Panel (C) shows a photograph showing the expression of a protein encoded by the human MUC gene analyzed via immunohistochemical staining.

When MUC1 was subjected to immunohistochemical staining aimed at inspection of protein expression, a novel anti-MUC1 antibody against "MUC1 cytoplasmic tail" (derived from the MUC1-common hybridoma (clone 014E) (JP Patent Application No. 2010-028729; Accession Number: NITE P-867, hereafter, referred to as "MUC1-014E") was also used, in addition to the conventional anti-MUC1 antibody (i.e., MUC1-DF3, manufactured by TFB). The anti-MUC2 antibody (MUC2-Ccp58, manufactured by Novo) was used regarding MUC2. Further, MUC4 was analyzed with the use of both the anti-MUC4 antibody (MUC4-8G7, University of Nebraska Medical Center, Omaha) reacting with the N-terminal subunit and the anti-MUC4 antibody (MUC4-1G8, Zymed) reacting with the C-terminal subunit. The same antibodies were used in Examples 6 to 9.

The methylation level of a methylated region associated with human MUC1, MUC2, and MUC4 gene promoter expression is substantially inversely correlated to mRNA and protein expression of such genes.

As shown in FIG. 8, the results of the MSE method regarding a methylated region associated with MUC1 gene promoter expression were not consistent with the results of staining of the conventional anti-MUC1 antibody (i.e., MUC1-DF3). However, such results were highly correlated with the measured MUC1 mRNA levels via RT-PCR and the results of immunohistochemical staining of "MUC1-014E." This demonstrates that methylation of the MUC1 gene can be analyzed by the MSE method using human colon samples prepared via crypt isolation.

As shown in FIG. 9, the results of the MSE method regarding a methylated region associated with MUC2 gene promoter expression indicate that a majority of normal mucosa samples of the large bowel exhibits a "low methylation level." Such results were consistent with the MUC2 mRNA levels measured by RT-PCR and with positive findings of MUC2. In contrast, a majority of cancer tissue samples exhibits a "low methylation level," which was approximately consistent with the MUC2 mRNA levels measured by RT-PCR, although a large number of samples were not consistent with the results of immunohistochemical staining of MUC2. Accordingly, such finding is considered to demonstrate that MUC2 protein expression in cancer tissue samples of the large bowel is influenced by the "post-transcriptional" factor after the expression of MUC2 mRNA. As described above, the results of the MSE method regarding a methylated region associated with MUC2 gene promoter expression were substantially consistent with the expression of MUC2 mRNA. This indicates that methylation of the MUC2 gene can be analyzed by the MSE method.

As shown in FIG. 10, the results of the MSE method regarding a methylated region associated with MUC4 gene promoter expression exhibit the "low methylation level" in all normal mucosa samples of the large bowel and cancer tissue samples of the large bowel, and such results were consistent with the MUC4 mRNA levels measured by RT-PCR. However, some cases were not consistent with the results of immunohistochemical staining of "MUC4-8G7." Such finding is considered to indicate that MUC4 protein expression in the cancer tissue samples of the large bowel is influenced by the "post-transcriptional" factor after the expression of MUC4 mRNA. As described above, the results of the MSE method regarding a methylated region associated with MUC4 gene promoter expression were completely consistent with MUC4 mRNA expression. This demonstrates that methylation of the MUC4 gene can be analyzed by the MSE method.

As shown in FIGS. 8 to 10, high mRNA expression levels were observed in all samples that exhibited a low methylation level by the MSE method. In addition, the methylation level was highly correlated with protein expression. Thus, methylation can be analyzed by the MSE method using human colon samples prepared via crypt isolation.

Example 6

Comparison of Methylation Analysis of Methylated Region Associated with Human MUC1, MUC2, and MUC4 Gene Promoter Expression in Human Tissue Samples Obtained via Surgery via MSE and Expression Analysis of Proteins Encoded by Such Genes via Immunohistochemical Staining Samples obtained from tumor regions and normal tissue of the human large bowel cancer and of pancreatic cancer via surgery were subjected to the methylation analysis of a methylated region associated with human MUC1 (FIG. 11), MUC2 (FIG. 12), and MUC4 (FIG. 13) gene promoter expression by the MSE method in the same manner as in Examples 1 to 3. Also, expression of proteins encoded by such genes was inspected via immunohistochemical staining. The results of such analyses were compared.

Figure 11:
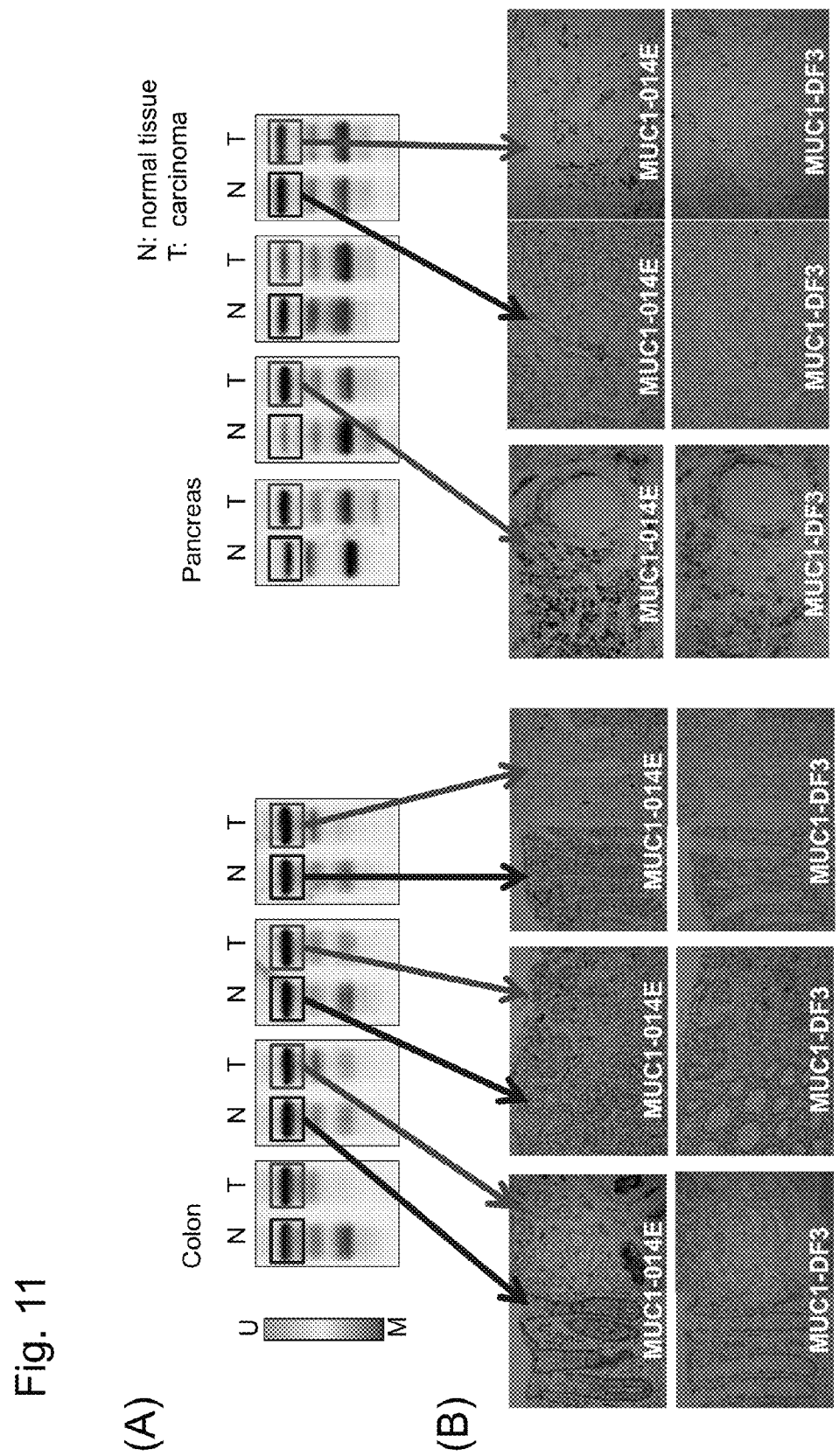
FIG. 11 shows a comparison of the results of methylation analysis of a methylated region associated with human MUC1 gene promoter expression in human tissue samples obtained via surgery by the method of the present invention and expression analysis of a protein encoded by such gene via immunohistochemical staining.
Figure 12:
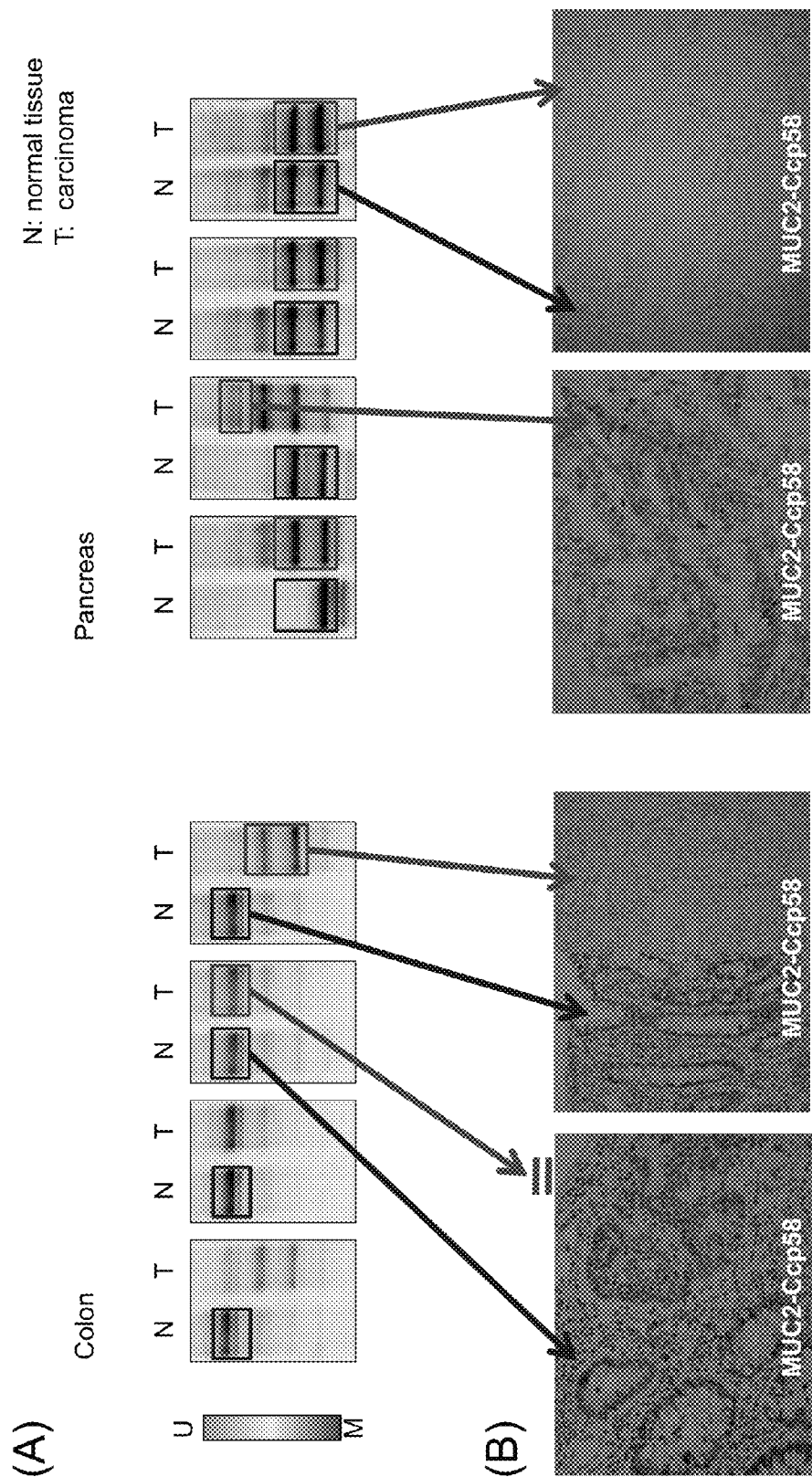
FIG. 12 shows a comparison of the results of methylation analysis of a methylated region associated with human MUC2 gene promoter expression in human tissue samples obtained via surgery by the method of the present invention and expression analysis of a protein encoded by such gene via immunohistochemical staining.

The results are shown in FIGS. 11 to 13. In FIGS. 11 to 13, "N" indicates a normal tissue sample and "T" indicates a cancer tissue sample. Panel (A) shows a photograph of a gel after DGGE analyzed by the MSE method. The gradient of a denaturing agent in a gel is adjusted to increase in the direction from the cathode to the anode of electrophoresis (from the top toward the bottom in the panel). Accordingly, "U" indicates "unmethylation" and "M" indicates "methylation." Panel (B) shows a photograph showing the expression of a protein encoded by the human MUC gene analyzed via immunohistochemical staining.

As shown in FIG. 11, the results of the MSE method regarding a methylated region associated with MUC1 gene promoter expression were not consistent with the results of staining of the conventional anti-MUC1 antibody (MUC1-DF3) in normal tissue, and such results were occasionally inconsistent with the results in tumor regions. However, such results were highly correlated with stainability of "MUC1-014E" that is considered to reflect MUC1 mRNA expression. This demonstrates that methylation of the MUC1 gene can be analyzed by the MSE method using human tissue samples obtained via surgery.

As shown in FIG. 12, the results of the MSE method regarding a methylated region associated with MUC2 gene promoter expression were inconsistent in some cancer tissue samples of the large bowel, although a high degree of correlation was found in most samples. In the case of the normal mucosa of the large bowel that was constantly positive for MUC2, all samples exhibited "low methylation level" as with the case of the samples prepared via crypt isolation shown in FIG. 9. All normal pancreatic tissue samples that were constantly negative of MUC2 exhibited "high methylation level" and pancreatic cancer tissue samples that were constantly negative of MUC2 exhibited "high methylation level." In the pancreatic cancer tissue samples in which intestinal metaplasia exceptionally occurred in part of the gastric cancer gland, a band exhibiting a "low methylation level" was observed. This demonstrates that methylation of the MUC2 gene can be analyzed by the MSE method using human tissue samples obtained via surgery.

As shown in FIG. 13, the results of the MSE method regarding a methylated region associated with MUC4 gene promoter expression were highly correlated with the results of immunohistochemical staining conducted with the use of the MUC4-8G7 antibody reacting with the N-terminal subunit and the MUC4-1G8 antibody reacting with the C-terminal subunit. This demonstrates that methylation of the MUC4 gene can be analyzed by the MSE method using the human tissue samples obtained via surgery.

Example 7

Comparison of Methylation Analysis of Methylated Region Associated with Human MUC1, MUC2, and MUC4 Gene Promoter Expression in Intracystic Liquid Samples of Cystic Tumors of Human Pancreas and in Pancreatic Fluid Samples of Pancreatic Cancer Cases via MSE and Expression Analysis of Proteins Encoded by Such Genes via Immunohistochemical Staining The intracystic liquid samples of a surgical case of an intraductal papillary mucinous neoplasm of the intestinal type (IPMN-intestinal), which is the cystic tumor of the human pancreas, or the pancreatic fluid samples obtained via retrograde pancreatography from pancreatic cancer (PDAC) cases were subjected to the methylation analysis of a methylated region associated with human MUC1, MUC2, and MUC4 gene promoter expression by the MSE method in the same manner as in Examples 1 to 3. In addition, expression of proteins encoded by such genes in the original tumor tissue was inspected via immunohistochemical staining, and the results were compared.

Figure 14:
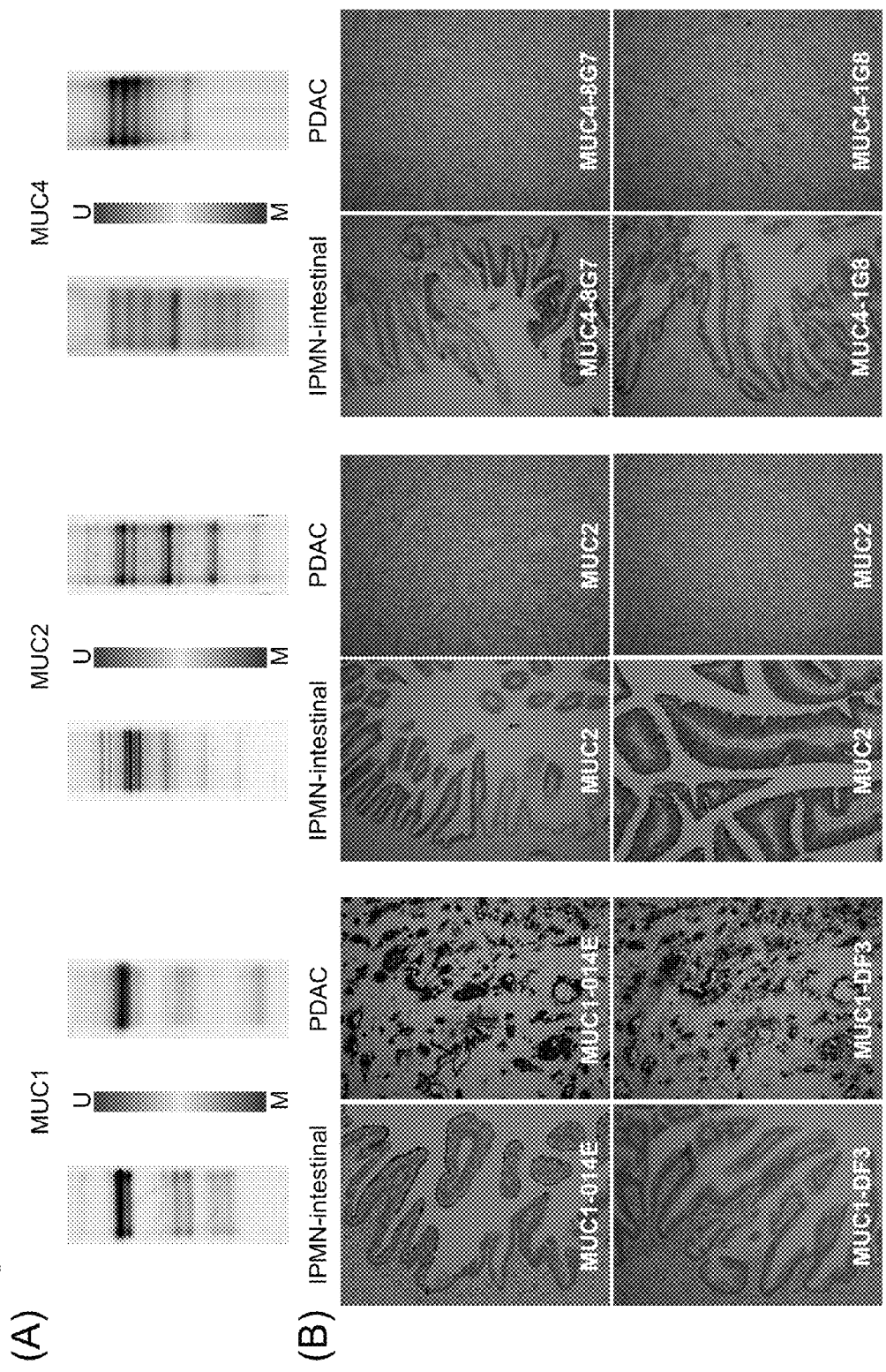
FIG. 14 shows a comparison of the results of methylation analysis of a methylated region associated with human MUC1, MUC2, and MUC4 gene promoter expression in intracystic liquid samples of cystic tumors of the human pancreas and in the pancreatic fluid samples of pancreatic cancer cases by the method of the present invention and expression analysis of a protein encoded by such gene via immunohistochemical staining.

The results are shown in FIG. 14. In FIG. 14, Panel (A) shows a photograph of a gel after DGGE conducted by the MSE method. The gradient of a denaturing agent in a gel is adjusted to increase in the direction from the cathode to the anode of electrophoresis (from the top toward the bottom in the panel). Accordingly, "U" indicates "unmethylation" and "M" indicates "methylation." Panel (B) shows a photograph showing the expression of a protein encoded by the human MUC gene analyzed via immunohistochemical staining.

As shown in the left panel of FIG. 14, the results of the MSE method regarding the methylated region associated with MUC1 gene promoter expression indicate a "low methylation level" in both of the IPMN-intestinal cases and the PDAC cases. Even when the results were not consistent with the results of staining of a conventional anti-MUC1 antibody (i.e., MUC1-DF3), the results were consistent with the results of staining positive for MUC1-014E, which is considered to reflect MUC1 mRNA expression.

As shown in the central panel of FIG. 14, the results of the MSE method regarding the methylated region associated with MUC2 gene promoter expression indicate a "low methylation level" in the case of the IPMN-intestinal type, and the results were consistent with the results of staining positive for MUC2. However, the results regarding the PDAC cases mainly exhibiting a "low methylation level" were not consistent with the results of staining negative for MUC2.

As shown in the right panel of FIG. 14, the results of the MSE method regarding the methylated region associated with MUC4 gene promoter expression exhibit many bands from "low methylation levels" to "high methylation levels" in the IPMN-intestinal cases. Such results were correlated with the results of immunohistochemical staining positive and negative for MUC4-8G7. The results regarding the PDAC cases exhibiting a "low methylation level" were consistent with the results of staining positive for "MUC4-1G8."

The above results demonstrate that methylation analysis by the MSE method may be useful for intracystic liquid samples of cystic tumors of the human pancreas (IPMN-intestinal) or pancreatic fluid samples obtained from pancreatic cancer cases.

Example 8

Comparison of Methylation Analysis of Methylated Region Associated with Human MUC1, MUC2, and MUC4 Gene Promoter Expression in Intracystic Liquid Samples of Cystic Tumors of Human Pancreas and in Pancreatic Fluid Samples of Pancreatic Cancer Cases via MSE and Expression Analysis of Proteins Encoded by Such Genes via Immunohistochemical Staining Intracystic liquid samples of a surgical case of the human intraductal papillary mucinous neoplasm of the gastric type (IPMN-gastric) were subjected to the methylation analysis of a methylated region associated with human MUC1, MUC2, and MUC4 gene promoter expression by the MSE method in the same manner as in Examples 1 to 3. Further, expression of proteins encoded by such genes in the original tumor tissue was inspected via immunohistochemical staining, and results were compared. The results regarding PDAC are as shown in FIG. 14.

Figure 15:
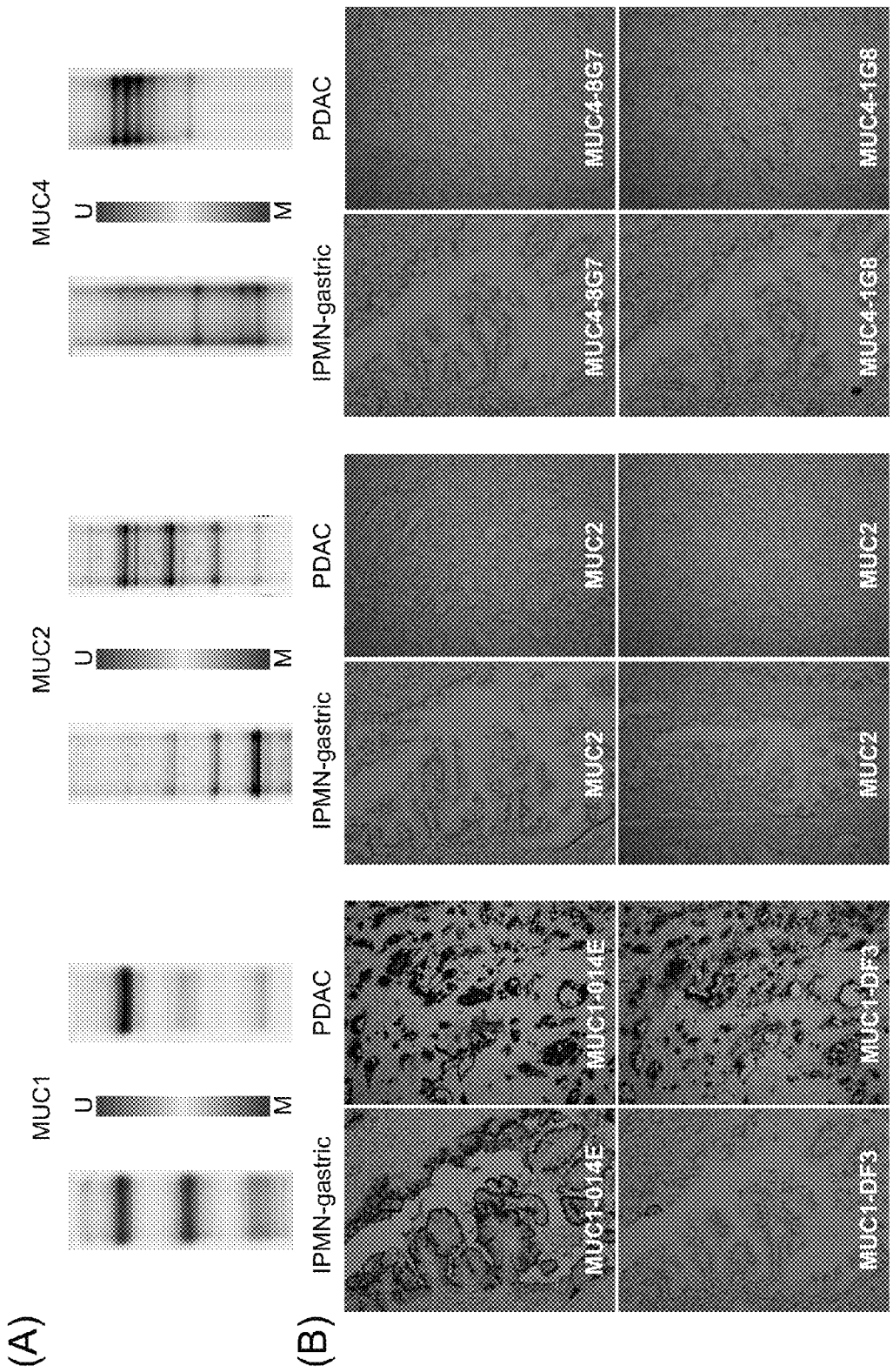
FIG. 15 shows a comparison of the results of methylation analysis of a methylated region associated with human MUC1, MUC2, and MUC4 gene promoter expression in the intracystic liquid samples of cystic tumors of the human pancreas and in the pancreatic fluid samples of pancreatic cancer cases by the method of the present invention and expression analysis of a protein encoded by such gene via immunohistochemical staining.

The results are shown in FIG. 15. In FIG. 15, Panel (A) shows a photograph of a gel after DGGE conducted by the MSE method. The gradient of a denaturing agent in a gel is adjusted to increase in the direction from the cathode to the anode of electrophoresis (from the top toward the bottom in the panel). Accordingly, "U" indicates "unmethylation" and "M" indicates "methylation." Panel (B) shows a photograph showing the expression of a protein encoded by the human MUC gene analyzed via immunohistochemical staining.

As shown in the left panel of FIG. 15, the results of the MSE method regarding the methylated region associated with MUC1 gene promoter expression show bands exhibiting a "low methylation level" and a "high methylation level" of the IPMN-gastric cases. While the band exhibiting a "low methylation level" was correlated with the results of staining positive for "MUC1-014E," the band exhibiting a "high methylation level" was not correlated therewith.

As shown in the central panel of FIG. 15, the results of the MSE method regarding the methylated region associated with MUC2 gene promoter expression exhibit a "high methylation level" in the IPMN-gastric cases, and such results were consistent with the results of staining negative for MUC2.

As shown in the right panel of FIG. 15, the results of the MSE method regarding the methylated region associated with MUC4 gene promoter expression exhibit a "high methylation level" in the IPMN-gastric cases, and such results were consistent with the results of staining negative for both "MUC4-8G7" and "MUC4-1G8."

The results demonstrate that methylation analysis by the MSE method may be useful for intracystic liquid samples of cystic tumors of the human pancreas (IPMN-gastric) or pancreatic fluid samples obtained from pancreatic cancer cases.

Example 9

Comparison of Methylation Analysis of Methylated Region Associated with Human MUC1, MUC2, and MUC4 Gene Promoter Expression in Intracystic Liquid Samples of Cystic Neoplasms of Human Bile Duct and Bile Samples of Extrahepatic Bile Duct Cancer (EHBDC) via MSE and Expression Analysis of Proteins Encoded by Such Genes via Immunohistochemical Staining Intracystic liquid samples of a surgical case of human mucin-producing bile duct tumor of the columnar type (MPBT-columnar) or bile samples in the gallbladder of cystic-duct-invading extrahepatic bile duct cancer (EHBDC) were subjected to the methylation analysis of a methylated region associated with human MUC1, MUC2, and MUC4 gene promoter expression by the MSE method in the same manner as in Examples 1 to 3. Further, expression of proteins encoded by such genes in the original tumor tissue was inspected via immunohistochemical staining, and results were compared.

Figure 16:
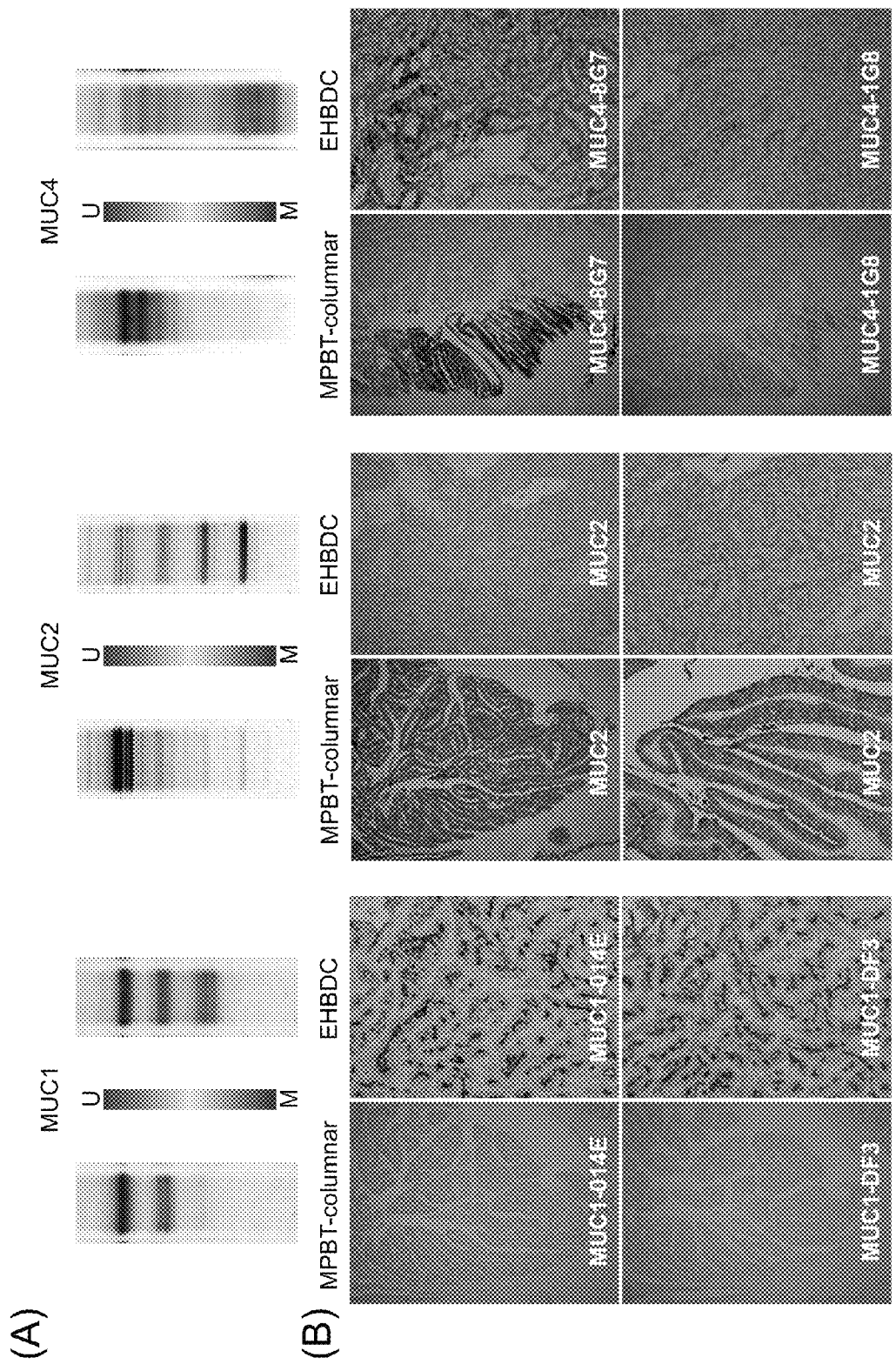
FIG. 16 shows a comparison of the results of methylation analysis of a methylated region associated with human MUC1, MUC2, and MUC4 gene promoter expression in the intracystic liquid samples obtained from cystic neoplasms of the human bile duct and in bile samples of extrahepatic bile duct cancer (EHBDC) cases by the method of the present invention and expression analysis of a protein encoded by such gene via immunohistochemical staining.

The results are shown in FIG. 16. In FIG. 16, Panel (A) shows a photograph of a gel after DGGE conducted by the MSE method. The gradient of a denaturing agent in a gel is adjusted to increase in the direction from the cathode to the anode of electrophoresis (from the top toward the bottom in the panel). Accordingly, "U" indicates "unmethylation" and "M" indicates "methylation." Panel (B) shows a photograph showing the expression of a protein encoded by the human MUC gene analyzed via immunohistochemical staining.

As shown in the left panel of FIG. 16, the results of the MSE method regarding the methylated region associated with MUC1 gene promoter expression exhibit a "low methylation level" in the case of the MPBT-columnar cases. Such results were not correlated with the results of staining negative for both original tumor tissue samples; i.e., MUC1-DF3 and MUC1-014E. In the case of EHBDC, however, a band exhibiting a "low methylation level" was consistent with the results of staining positive for both original tumor tissue samples; i.e., MUC1-DF3 and MUC1-014E, and a band exhibiting behavior similar to a "high methylation level" was also observed.

As shown in the central panel of FIG. 16, the results of the MSE method regarding the methylated region associated with MUC2 gene promoter expression exhibit a "low methylation level" in the MPBT-columnar cases, and such results were consistent with the results of staining positive for MUC2. The results exhibit a "high methylation level" in the case of EHBDC, which were consistent with the results of staining negative for MUC2.

As shown in the right panel of FIG. 16, the results of the MSE method regarding the methylated region associated with MUC4 gene promoter expression exhibit a "low methylation level" in the MPBT-columnar cases, and such results were correlated with the results of immunohistochemical staining positive for both "MUC4-8G7" and "MUC4-1G8." In the case of EHBDC, many bands from "low methylation levels" to "high methylation levels" were observed, and such results were correlated with the results of immunohistochemical staining positive and negative for "MUC4-8G7" and "MUC4-1G8."

The above results indicate that methylation analysis by the MSE method may be useful for intracystic liquid samples of cystic neoplasms of the human bile duct (MPBT-columnar) and for bile samples of extrahepatic bile duct cancer, although there is a certain degree of inconsistency.

Example 10

Evaluation of Influence of Formalin-Fixation Time and Paraffin-Embedding Time on DNA Methylation via MSE Example 10 demonstrates that the influence of the formalin-fixation time and the paraffin-embedding time on DNA methylation can be precisely elucidated by the MSE method.

Formalin-fixed, paraffin-embedded pathological samples are excellent in storage stability, and past cases can be genetically screened with the use thereof. Accordingly, genetic analysis involving the use of, for example, microdissected samples of formalin-fixed, paraffin-embedded pathological samples, has become actively implemented. However, whether or not the formalin-fixation time or paraffin-embedding time affects DNA methylation has not yet been sufficiently examined.

Thus, the influence of the formalin-fixation time and the paraffin-embedding time on DNA methylation was analyzed by the MSE method and by the MSP method. The normal mucosa tissue of the human large bowel that was analyzed in terms of the expression conditions and the DNA methylation status of mucin to accumulate the data so far was used as a sample, and the methylation analysis of methylated regions each associated with mucin (MUC1, MUC2, and MUC4) gene promoter expression was carried out by the MSE method in the same manner as in Examples 1 to 3.

MUC1 was analyzed by the MSP method using a set of primers: MSP-UL (GGGGATTGGTATAAAGTGGTAGGT: SEQ ID NO: 17); MSP-UR (AAAACAAAACAATTCAAA-CAAACA:SEQ ID NO: 18); MSP-ML (GATCGG-TATAAAGCGGTAGGC: SEQ ID NO: 19); and MSP-MR (AAAACAAAACAAATTCAAACAAACG: SEQ ID NO: 20) with reference to the literature (Norishige Yamada, Yukari Nishida, Hideaki Tsutsumida, Tomofumi Hamada, Masamichi Goto, Michiyo Higashi, Mitsuharu Nomoto, and Suguru Yonezawa, 2008, MUC1 expression is regulated by DNA methylation and histone H3-K9 modification in cancer cells, Cancer Res., 68 (8): 2708-16).

MUC2 was analyzed by the MSP method using a set of primers: MSP-UL (GTTGTTTTATTTTGAAGAAGGT-TGTG: SEQ ID NO: 21); MSP-UR (TAACAAAAA-CAATATAAATTACACCCAAA: SEQ ID NO: 22); MSP-ML (GTTGTTTTATTTTGAAGAAGGTTGC: SEQ ID NO: 23); and MSP-MR (CGATATAAATTACGCCCGAA: SEQ ID NO: 24) with reference to the literature (Norishige Yamada, Tomofumi Hamada, Masamichi Goto, Hideaki Tsutsumida, Michiyo Higashi, Mitsuharu Nomoto, and Suguru Yonezawa, 2006, MUC2 expression is regulated by histone H3 modification and DNA methylation in pancreatic cancer, Int. J. Cancer, 119 (8): 1850-7).

MUC4 was analyzed by the MSP method using a set of primers: MSP-UL (GGTGATTAGTGTGGGGTTTTG: SEQ ID NO: 25); MSP-UR (CCAAACCAAATACATTTCTC-CAA: SEQ ID NO: 26); MSP-ML (GGTGATT-AGCGTGGGGTTTC: SEQ ID NO: 27); and MSP-MR (CGAACCAAATACGTTTCTCCG:SEQ ID NO: 28) with reference to the literature (Norishige Yamada, Yukari Nishida, Hideaki Tsutsumida, Masamichi Goto, Michiyo Higashi, Mitsuharu Nomoto, and Suguru Yonezawa, 2009, Promoter CpG methylation in cancer cells contributes to regulation of MUC4, Br. J. Cancer, 100 (2): 344-51).

Figure 17:
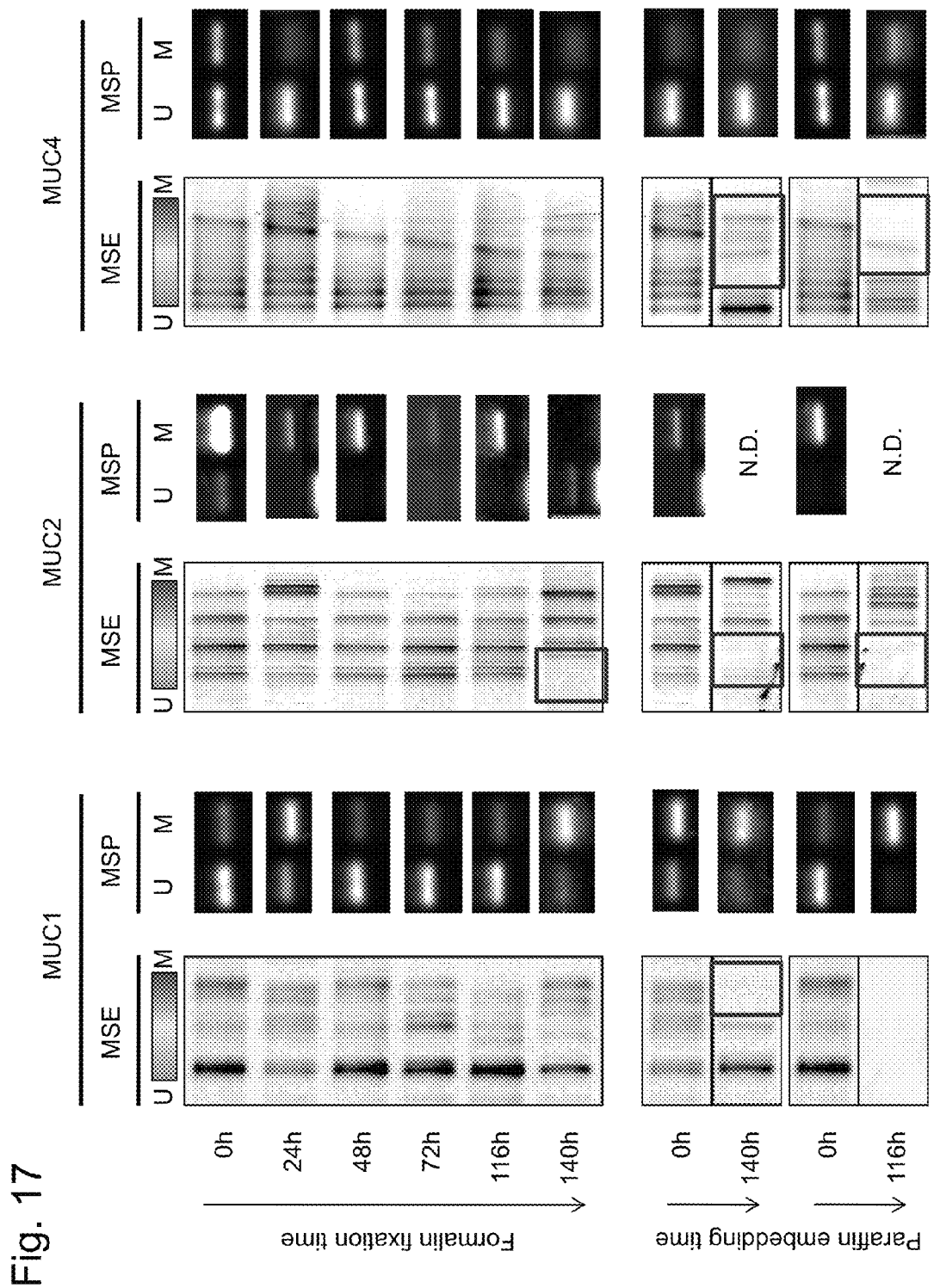
FIG. 17 shows the results of evaluation by the method of the present invention regarding the influence of the formalin-fixation time and the paraffin-embedding time on DNA methylation.

As shown in FIG. 17, the normal mucosa tissue samples of the human large bowel were fixed to formalin up to 140 hours by dividing the fixation time. All samples were fixed to formalin for 24 or 48 hours, embedded in paraffin, and then analyzed by the MSE method and by the MSP method. The results are shown in FIG. 17. The gradient of a denaturing agent in a gel used in the MSE method is adjusted to increase in the direction from the cathode to the anode of electrophoresis (from the left toward the right in the panel). "U" indicates "unmethylation" and "M" indicates "methylation." In the panel showing the results of MSP, "U" indicates "unmethylation" and "M" indicates "methylation."

(1) Influence of Formalin-Fixation Time on DNA Methylation

According to the analysis implemented by the MSE method, no influence of formalin fixation was observed up to 140 hours in the target regions of the MUC1 and MUC4 genes. While no influence of formalin fixation was observed up to 116 hours in the target region of the MUC2 gene, a band exhibiting a "low methylation level" disappeared from the sample that had been fixed to formalin for 140 hours.

According to the analysis implemented by the MSP method, the obvious influence of formalin fixation and paraffin embedding as observed by the MSE method could not be analyzed.

The results demonstrate that the influence of the duration for treatment of target region should be examined when a formalin-fixed sample is subjected to DNA methylation analysis.

(2) Influence of Formalin Fixation Followed by Paraffin Embedding on DNA Methylation The methylation analysis of a methylated region associated with mucin gene promoter expression was carried out using samples that had been fixed to formalin and then embedded in paraffin for 24 or 48 hours. A methylation status in a target region did not change in samples that had been subjected to deparaffinization immediately after paraffin embedding and DNA purification.

However, disappearance of a band exhibiting a "high methylation level" was observed in the methylated region associated with MUC1 and MUC4 gene promoter expression via analysis by the MSE method using a sample obtained from a paraffin block that was allowed to stand at room temperature for 116 or 140 hours after paraffin embedding. Also, disappearance of a band exhibiting a "low methylation level" was observed in the methylated region associated with MUC2 gene promoter expression.

When similar analysis was carried out by the MSP method, stable results could not be obtained, and the obvious influence of formalin fixation and paraffin embedding as observed by the MSE method could not be analyzed.

The results demonstrate that the influence of changes with the elapse of time in a target region should be examined when a formalin-fixed, paraffin-embedded sample is subjected to methylation analysis.

The above results provide a warning regarding the easy implementation of DNA methylation analysis with the use of a formalin-fixed, paraffin-embedded sample that has been stored for a long period of time.

The results demonstrated in Examples 5 to 9 indicate that samples obtained via surgery such as body fluid samples (e.g., pancreatic juice and bile) derived from a human can be analyzed by the MSE method, and this method is considered to be actually effective for early diagnosis of cancer in a human. As shown in Example 10, the MSE method is capable of elucidating the influences of formalin fixation or paraffin embedding of samples on DNA methylation, which could not be defined by the conventional MSP method or other methods.

Example 11

Methylation Analysis of Methylated Region Associated with Mucin Core Protein 5AC (MUC5AC) Gene Promoter Expression via MSE In Example 11, methylation of a methylated region associated with human MUC5AC gene promoter expression was analyzed by the MSE method. FIG. 18 shows a sequence of a methylated region associated with human MUC5AC gene promoter expression (SEQ ID NO: 29; the DNA sequence after bisulfite treatment, and uracil converted from unmethylated cytosine is indicated as "thymine"). In FIG. 18, "TG" indicated by boldface that is framed by a square indicates the CpG site that is important for human MUC5AC gene promoter expression, and other "TGs" framed by squares indicate other CpG sites. "T" indicated by italic face represents "T" converted from "C" via bisulfite treatment.

11-1. Sample Preparation and Method

In the same manner as in Example 1, DNA samples were extracted from the cell strains indicated below using the DNeasy Blood & Tissue Kit (Qiagen): MCF-7, T-47D, MDA-MB-453, NCI-H292, A427, BxPC3, HPAF II, PANC1, LS174T, and Caco2, and the extracted DNA samples were subjected to bisulfite treatment using EpiTect Bisulfite Kits (Qiagen).

The DNA samples after bisulfite treatment were subjected to PCR performed with the use of the primers shown below. Set of primers (the nucleotide sequence indicated by lower-case letters is the GC clamp):

Primer 5-1:
(SEQ ID NO: 30)
5'-AAAGTTTTGGGTGTGTGGAG-3';

Primer 5-2:
(SEQ ID NO: 31)
5'-ATCAATATCCAACCCCCAAC-3';

Primer 5-3:
(SEQ ID NO: 32)
5'-cgcccgccgcgcgcggcgggcggggcggggcacggggggTTTATGTTTAGGGGTTTTGG-3';
and Primer 5-4:
(SEQ ID NO: 33)
5'-ACCAACTAACCACCCAAACC-3'

As shown in FIG. 18, the 1$^{st}$ PCR was carried out with the use of Primer 5-1 and Primer 5-2, and the 2$^{nd}$ PCR (nested PCR) was carried out with the use of Primer 5-3 and Primer 5-4. The AmpliTaq Gold® Fast PCR Master Mix (Applied Biosystem) was used as polymerase. PCR conditions and temperature conditions are shown in Table 7.

TABLE 7

Composition of reaction solution for 1$^{st}$ PCR

| DNA after bisulfite treatment | 1 µl |
|---|---|
| Master Mix | 10 µl |
| Primer 5-1 | 0.3 µl |
| Primer 5-2 | 0.3 µl |
| dH$_2$O | 8.4 µl |
| Total | 20 µl |

1$^{st}$ PCR temperature conditions

| 95° C. | 10 min | |
|---|---|---|
| 96° C. | 5 sec | |
| 62° C. | 5 sec | 40 cycles |
| 68° C. | 9 sec | |
| 72° C. | 10 sec | |

Composition of reaction solution for 2$^{nd}$ PCR

| 1$^{st}$ PCR amplicon | 2 µl |
|---|---|
| Master Mix | 10 µl |
| Primer 5-3 | 0.3 µl |
| Primer 5-4 | 0.3 µl |
| dH$_2$O | 7.4 µl |
| Total | 20 µl |

2$^{nd}$ PCR temperature conditions

| 95° C. | 10 min | |
|---|---|---|
| 96° C. | 5 sec | |
| 62° C. | 5 sec | 45 cycles |

TABLE 7-continued

| 68° C. | 9 sec |
|---|---|
| 72° C. | 10 sec |

Subsequently, the reaction solution after the 2$^{nd}$ PCR was subjected to DGGE using a denaturing gradient gel having the conditions for DGGE gel shown in Table 8. Electrophoresis was carried out in an electrophoresis bath at 60° C. at a constant voltage of 230 V for 300 minutes. The Dcode System (BIO-RAD) was used as an electrophoresis bath.

TABLE 8

Conditions for DGGE gel

10% acrylamide gel
Denaturing density gradient: 30% to 40%

Composition of 30% denaturing gel

| 40% stock solution | 3.0 ml |
|---|---|
| 50x TAE buffer | 0.3 ml |
| Urea | 1.88 g |
| Formamide | 1.8 ml |

Composition of 40% denaturing gel

| 40% stock solution | 3.0 ml |
|---|---|
| 50x TAE buffer | 0.3 ml |
| Urea | 2.51 g |
| Formamide | 2.4 ml |

40% stock solution: Bio-Rad, 40 (w/v)% acrylamide/bis mixed solution (37.5:1);
50x TAE buffer: Nacalai Tesque, Tris-acetate-EDTA buffer (50x);
Urea: Nacalai Tesque, SP grade;
Formamide: Nacalai Tesque, SP grade 11-2. Results of Analysis FIG. 19 shows the results of analysis of the cell strains. Panel (A) shows the results of evaluation of methylation in a methylated region associated with human MUC5AC gene promoter expression of the cell strains by the MassARRAY method. A region framed by a rectangle is the target region of Example 11 (i.e., the CpG sites). Panel (B) shows a photograph of a gel after DGGE conducted in Example 11. The gradient of a denaturing agent in a gel is adjusted to increase in the direction from the cathode to the anode of electrophoresis (from the top toward the bottom in the panel).

As shown in FIG. 19, the results of evaluation of methylation by the MSE method were highly correlated with those by the MassARRAY method. As represented by a region framed by a square on the left side of Panel (A), a methylation status in a considerably upstream region around −3,700 of the MUC5AC gene was found to be correlated with mRNA, such correlation was confirmed via pyrosequencing and MSE, and all results were consistent with each other. In addition, histone modification was associated with MUC5AC gene expression in the upstream region.

Comparative Example 1

Comparison of Bisulfite-DGGE Method and MSE Method

Samples prepared by the conventional bisulfite-DGGE method were compared with samples prepared by the MSE method. DGGE was carried out with the use of an acrylamide gel involving a density gradient of a denaturing agent alone. A target of evaluation of DNA methylation is the methylated region associated with human MUC1 gene promoter expression, as in the case of Example 1.

According to the bisulfite-DGGE method, samples were prepared via conventional PCR procedures performed with the use of Primer 1-3 and Primer 1-4 of the set of primers described in Example 1 without performing nested PCR. The compositions of PCR reaction solutions and temperature conditions are in accordance with those of the $1^{st}$ PCR as shown in Table 1.

In the case of the MSE method, samples were prepared in the same manner as in Example 1.

Figure 20:
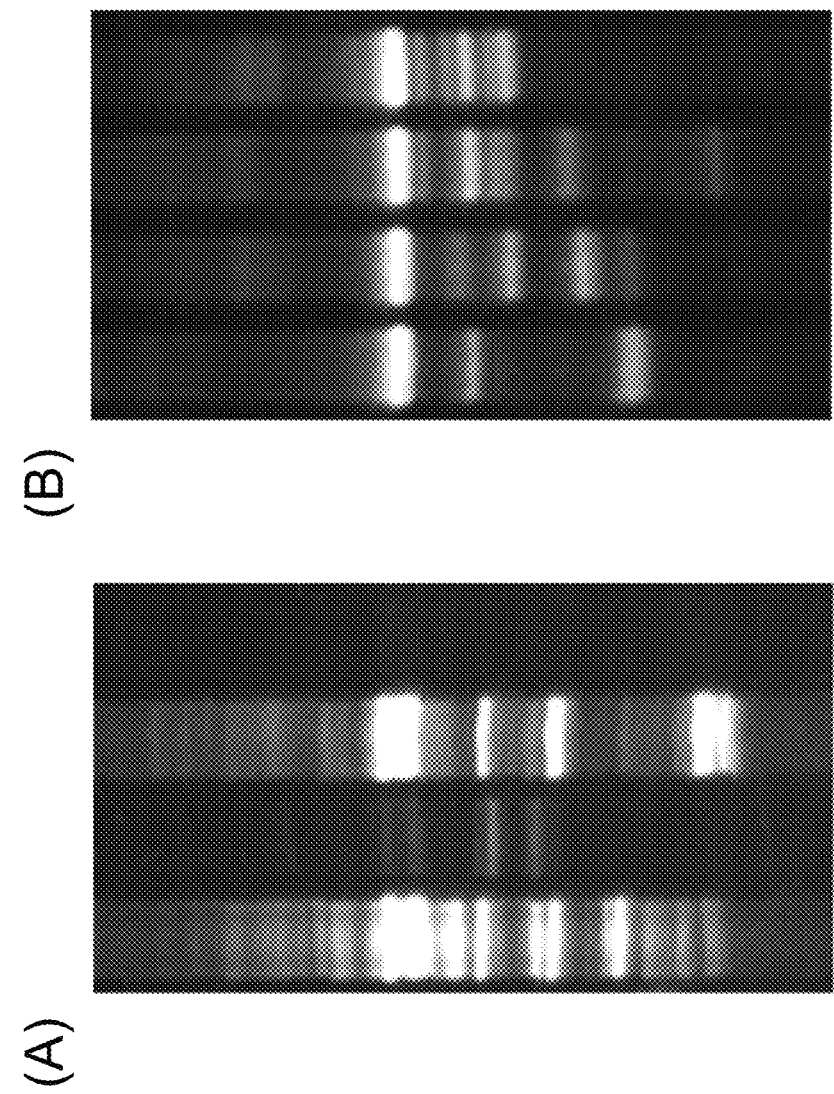
FIG. 20 shows the results of a comparison of the bisulfite-DGGE method and the method of the present invention.

The results are shown in FIG. 20. Panel (A) shows a photograph of a gel after DGGE by the bisulfite-DGGE method. Panel (B) shows a photograph of a gel after DGGE by the MSE method. The gradient of a denaturing agent in a gel is adjusted to increase in the direction from the cathode to the anode of electrophoresis (from the top toward the bottom in the panel).

As shown in FIG. 20, accurate analysis could not be carried out due to non-specific amplification or amplification of a non-targeted region resulting from bisulfite treatment by the bisulfite-DGGE method. Otherwise, amplification by PCR was not sufficiently carried out due to small amounts of samples, and a band could not be detected. In contrast, the MSE method yielded stable analysis results.

Figure 21:
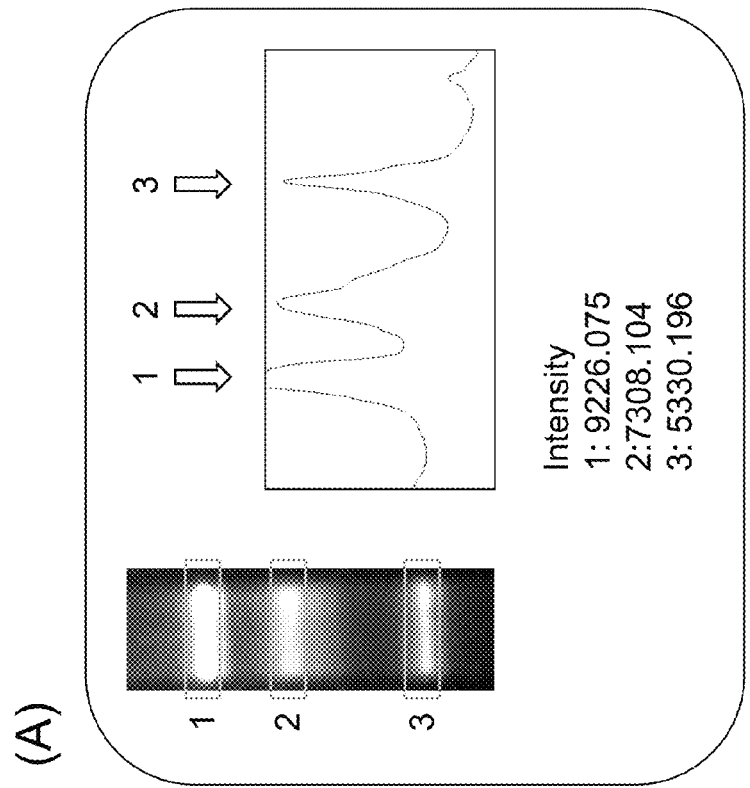
FIG. 21 shows the results of a comparison of the detection performance of the bisulfite-DGGE method and that of the method of the present invention in cell strains.
Figure 23:
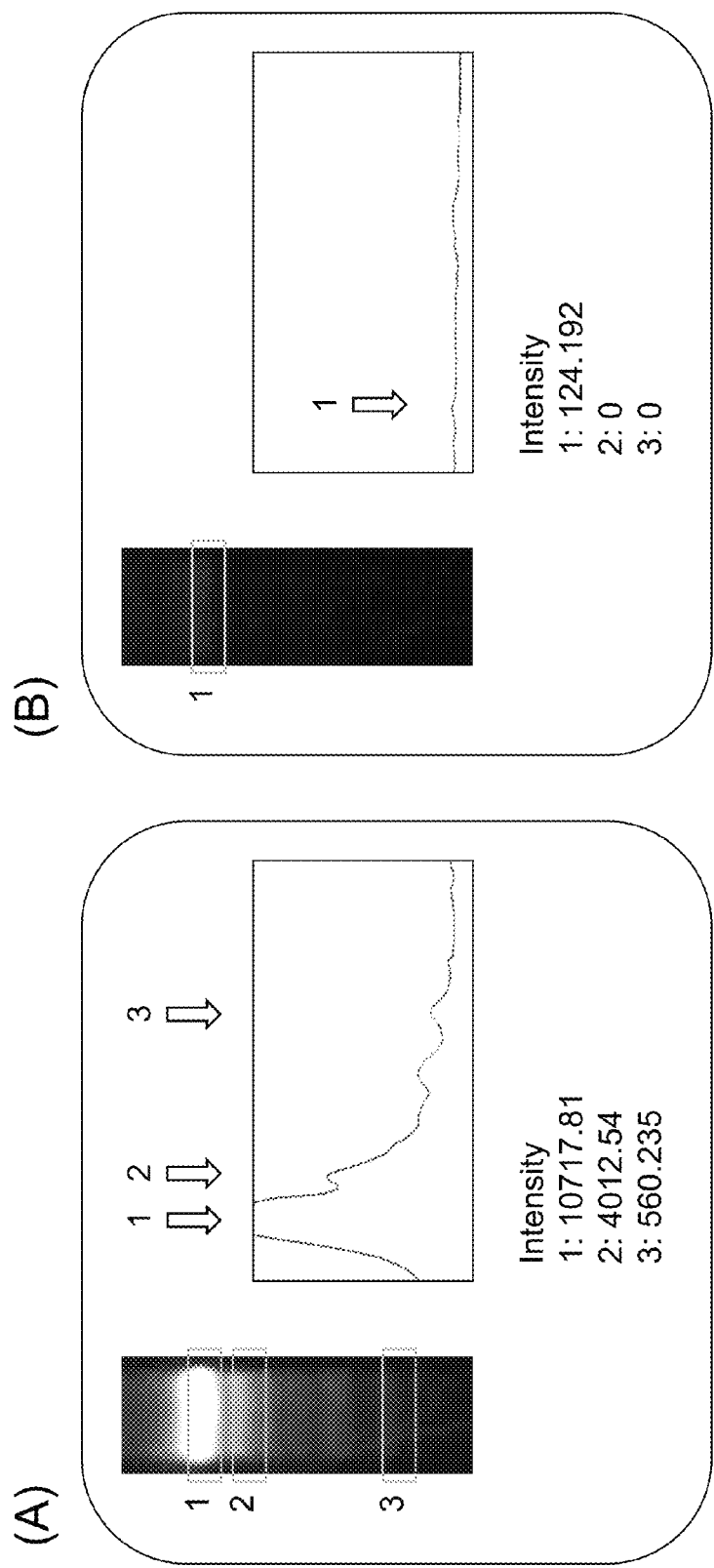
FIG. 23 shows the results of a comparison of the detection performance of the bisulfite-DGGE method and that of the method of the present invention in body fluid samples.

In order to compare the bisulfite-DGGE method with the MSE method, the emission intensity of a band of a gel after DGGE in the photograph was determined and calculated using Image J regarding the cell strain (FIG. 21), the tissue sample (FIG. 22), and the body fluid sample (FIG. 23). In FIGS. 21 to 23, Panel (A) shows the results regarding the MSE method, and Panel (B) shows the results regarding the bisulfite-DGGE method.

In addition, the results of comparison of the detection performance of the bisulfite-DGGE method and the MSE method are shown in Table 9 below. In Table 9, the ratio of the band emission intensity was calculated as the value indicated by: emission intensity measured via MSE method/the emission intensity measured via bisulfite-DGGE method.

TABLE 9

| Ratio of band emission intensity (MUC1 analysis) | | | | | | | | | | | |
|---|---|---|---|---|---|---|---|---|---|---|---|
| Cell strain samples | 8.0 | 42.4 | 25.1 | 10.4 | 11.0 | 104.6 | 10.7 | 64.3 | 50.9 | 13.0 | Average | 34.0 |
| Tissue samples | 39.9 | 32.5 | 68.7 | | | | | | | | Average | 47.0 |
| Body fluid samples | 18.7 | 76.3 | 30.0 | 86.3 | | | | | | | Average | 52.8 |
| | | | | | | | | | | | Overall average | 44.6 |

As shown in FIGS. 21 to 23 and Table 9, on average, the detection performance attained by the MSE method was greater than that attained by the bisulfite-DGGE method by 34 times in the case of cell strain samples, 47 times in the case of tissue samples, and 53 times in the case of body fluid samples. That is, the detection performance attained by the MSE method was 45 times (up to 105 times) greater on average than that attained by the bisulfite-DGGE method. The MSE method exhibited a higher detection performance than the bisulfite-DGGE method regarding a band that can be detected by both analytical methods.

INDUSTRIAL APPLICABILITY

According to the present invention, DNA methylation in trace amounts of DNA samples can be detected, and DNA methylation patterns or continuity can be detected.

Also, the method for detecting DNA methylation of the present invention can be effectively used in the life science field, such as epigenetics.

All publications, patents, and patent applications cited herein are incorporated herein by reference in their entirety.

SEQUENCE LISTING

<160> NUMBER OF SEQ ID NOS: 33

<210> SEQ ID NO 1
<211> LENGTH: 40

```
<212> TYPE: DNA
<213> ORGANISM: Artificial
<220> FEATURE:
<223> OTHER INFORMATION: GC-clamp

<400> SEQUENCE: 1
cgcccgccgc gcgcggcggg cggggcgggg gcacgggggg                           40

<210> SEQ ID NO 2
<211> LENGTH: 596
<212> TYPE: DNA
<213> ORGANISM: Artificial
<220> FEATURE:
<223> OTHER INFORMATION: Methylated region which is involved in
      expression of a promoter of human MUC1 gene and is bisulfite-
      treated, showing the urasil to which the unmethylated cytosine is
      converted as thymine

<400> SEQUENCE: 2
gggaagtgga gtgggagatt tagggtggg tttttgatt tgttgtata ggattttgat        60 ttagttggtt ttgttttta ttttatgtt agttgttgtt ttgaggttaa aattagagtt      120
taggggttta agtttagat tgtttttttt ttttttttg gagttaggga gtggttggtg     180 aaaggggag gttagttgga gaataaatgg gtagttaggg ggttgagtga ttagagttt     240 tgtattttat ttagaatggt tggggaggag gaggaagagg taggaggtag gggagggggt   300
ggggttttgt tatttgttat ttgttttggt tgtgtttagg gtgggtgggt ggggagtggg   360
gggattggta taaagtggta gtgtttgtgt ttgtttttatt ttttaagtag ttagtgtttg   420
tttgaatttg ttttgttttt ttttattta ttttattatt attatgatat tgggtattta     480 gtttttttt ttttgttgt tgttttttta gtgtttatag gtgaggggta tgaggtgggg    540
agtgggttgt tttgtttagg tggttttgt ggttttttg tgggttttgt tttttg          596

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3 aaaggggag gttagttgga                                                  20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
aaacaaccca ctccccacct                                                 20

<210> SEQ ID NO 5
<211> LENGTH: 60
<212> TYPE: DNA
<213> ORGANISM: Artificial
<220> FEATURE:
<223> OTHER INFORMATION: Primer

<400> SEQUENCE: 5
cgcccgccgc gcgcggcggg cggggcgggg gcacgggggg aagaggtagg aggtagggga    60
```

```
<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
aaaacaaaac aaattcaaac                                              20

<210> SEQ ID NO 7
<211> LENGTH: 497
<212> TYPE: DNA
<213> ORGANISM: Artificial
<220> FEATURE:
<223> OTHER INFORMATION: Methylated region which is involved in
      expression of a promoter of human MUC2 gene and is bisulfite-
      treated, showing the urasil to which the unmethylated cytosine is
      converted as thymine

<400> SEQUENCE: 7
gaaggatttt atatttttt tgtttttggg gaggttttt tttggggtta ggtttggaag    60
ttgttttaga gtttgggttt taggaatggg ttggtttttt tagtgtaatg tgagtttgat   120
taggtttggg atttgtttag tgggtgtttg ggggtttatg gtgggttaag gagtttgatt   180
agatttgttt ttggtaggat attttttttt tggttatttt gggtttgttt ttttagtagt   240
tgtatgtgtt ttttggtgtg tgttggtatt taggttatag ggttgttta ttttgaagaa    300 ggttgtgttt atttagggag ttataaagag atgattttg ataatttgaa ttaatatttt    360
tttattgggg tttgggtttt ttagttgttt ttttgattat ttggtagatg ttatatttat   420
ttttggtttt ttttgtttt tttgtttttt tatttttttg ttaggatata taaggattag    480 attttttgttt ttgggtg                                                497

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tttggggtta ggtttggaag                                              20

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
accttcttca aaataaaaca acc                                          23

<210> SEQ ID NO 10
<211> LENGTH: 60
<212> TYPE: DNA
<213> ORGANISM: Artificial
<220> FEATURE:
<223> OTHER INFORMATION: Primer

<400> SEQUENCE: 10
cgcccgccgc gcgcggcggg cggggcgggg gcacgggggg ttttagagtt tgggttttag   60
```

-continued

```
<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
taacctaaat accaacacac a                                          21

<210> SEQ ID NO 12
<211> LENGTH: 343
<212> TYPE: DNA
<213> ORGANISM: Artificial
<220> FEATURE:
<223> OTHER INFORMATION: Methylated region which is involved in
      expression of a promoter of human MUC4 gene and is bisulfite-
      treated, showing the urasil to which the unmethylated cytosine is
      converted as thymine

<400> SEQUENCE: 12
tagagtaatg ggtgtattgg tgttttttt tttggtgggg tagtggggtg gggttgagga      60
gagaaaaggg tgattagtgt ggggttttgt ttttttttgt ttttttttta ggttttttgg    120
tttttttgag aaatgtattt ggtttgggtt agttgtttga ggggatgggt ttatgtttgt    180
tttttatatt gtagttgttg ggttgtggag tttttttagg gagttagggg gattttttgtt  240 gtagttatga aggggtatgt tggaggaggg tttttttggg tgttttttgagt tgtttgtgtt  300 tttgttttttt tttgtatgtg gttttaggta agtgatggag ata                    343

<210> SEQ ID NO 13
<211> LENGTH: 17
<212> TYPE: DNA
<213> ORGANISM: Artificial
<220> FEATURE:
<223> OTHER INFORMATION: Primer

<400> SEQUENCE: 13
tagtggggtg gggttga                                               17

<210> SEQ ID NO 14
<211> LENGTH: 17
<212> TYPE: DNA
<213> ORGANISM: Artificial
<220> FEATURE:
<223> OTHER INFORMATION: Primer

<400> SEQUENCE: 14
aaacacccaa aaaaccc                                               17

<210> SEQ ID NO 15
<211> LENGTH: 60
<212> TYPE: DNA
<213> ORGANISM: Artificial
<220> FEATURE:
<223> OTHER INFORMATION: Primer

<400> SEQUENCE: 15
cgcccgccgc gcgcggcggg cggggcgggg gcacgggggg aggagagaaa agggtgatta     60

<210> SEQ ID NO 16
<211> LENGTH: 20
<212> TYPE: DNA
<213> ORGANISM: Artificial
<220> FEATURE:
<223> OTHER INFORMATION: Primer
```

<400> SEQUENCE: 16
acccaaaaaa ccctcctcca                                          20

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
ggggattggt ataaagtggt aggt                                     24

<210> SEQ ID NO 18
<211> LENGTH: 24
<212> TYPE: DNA
<213> ORGANISM: Artificial
<220> FEATURE:
<223> OTHER INFORMATION: primer

<400> SEQUENCE: 18
aaaacaaaac aattcaaaca aaca                                     24

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
gatcggtata aagcggtagg c                                        21

<210> SEQ ID NO 20
<211> LENGTH: 25
<212> TYPE: DNA
<213> ORGANISM: Artificial
<220> FEATURE:
<223> OTHER INFORMATION: primer

<400> SEQUENCE: 20
aaaacaaaac aaattcaaac aaacg                                    25

<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21
gttgttttat tttgaagaag gttgtg                                   26

<210> SEQ ID NO 22
<211> LENGTH: 29
<212> TYPE: DNA
<213> ORGANISM: Artificial
<220> FEATURE:
<223> OTHER INFORMATION: Primer

<400> SEQUENCE: 22
taacaaaaac aatataaatt acacccaaa                                29

<210> SEQ ID NO 23

```
<211> LENGTH: 25
<212> TYPE: DNA
<213> ORGANISM: Artificial
<220> FEATURE:
<223> OTHER INFORMATION: Primer

<400> SEQUENCE: 23
gttgttttat tttgaagaag gttgc                                           25

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cgatataaat tacgcccgaa                                                 20

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
ggtgattagt gtgggtttt g                                                21

<210> SEQ ID NO 26
<211> LENGTH: 23
<212> TYPE: DNA
<213> ORGANISM: Artificial
<220> FEATURE:
<223> OTHER INFORMATION: Primer

<400> SEQUENCE: 26
ccaaaccaaa tacatttctc caa                                             23

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
ggtgattagc gtgggtttc                                                  20

<210> SEQ ID NO 28
<211> LENGTH: 21
<212> TYPE: DNA
<213> ORGANISM: Artificial
<220> FEATURE:
<223> OTHER INFORMATION: Primer

<400> SEQUENCE: 28
cgaaccaaat acgtttctcc g                                               21

<210> SEQ ID NO 29
<211> LENGTH: 700
<212> TYPE: DNA
<213> ORGANISM: Artificial
<220> FEATURE:
<223> OTHER INFORMATION: Methylated region which is involved in
      expression of a promoter of human MUC5AC gene and is bisulfite-
      treated, showing the urasil to which the unmethylated cytosine is
``` converted as thymine

<400> SEQUENCE: 29

```
ttaggaggta ggtggttgtg ttatggtttg gttagttttg tttgtatttt ttgagagttt    60
ttagtaaggt tgtagtgatt attttagatt ttttttgag gtttgtggtg tggttgggat   120
tttattgttt tgggatat atagaaaatg tttatagagt ttagaaataa ggtttagtgg    180
gttttttgga aagttttggg tgtgtggagt ttggggttgt aggttttgga attgtaggta   240
ttggttttag gttttttgag gttttggttt ggtgggggttt ttatgggatt aggtggttag   300
tttgtggttt atgtttaggg gttttgggtg tttgagttta ggttttaaga ggaagtttag   360
tatagttagg ggttattaat attggtgggg ggaagttatt ttagttggat tttagtagtg   420
gttttgggtg atgtttggtt gagggaggag aaagttgtgg ttggggtggt aaggtttggg   480
tggttagttg gttaggtgtt ttggggtttg gtttagtttt agatatgtag ggggtatttt   540
tttttgaggg ttatgttggt gatttagatt gtttagaggt tatggtatgg attgggttag   600
tgatttaggt ttgttttttg ttggggttg gatattgatt tatttattgt ttttttgttta   660
tttgagggtg taaggagggt aggttttag gtatttatat                          700
```

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30

```
aaagttttgg gtgtgtggag                                               20
```

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31

```
atcaatatcc aaccccaac                                                20
```

<210> SEQ ID NO 32
<211> LENGTH: 60
<212> TYPE: DNA
<213> ORGANISM: Artificial
<220> FEATURE:
<223> OTHER INFORMATION: primer

<400> SEQUENCE: 32

```
cgcccgccgc gcgcggcggg cggggcgggg gcacgggggg tttatgttta ggggttttgg   60
```

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33

```
accaactaac cacccaaacc                                               20
```

The invention claimed is:

1. A method for detecting DNA methylation comprising steps of:
   subjecting DNA to bisulfite treatment;
   subjecting the DNA after bisulfite treatment to a first PCR using the first set of primers corresponding to outer regions of the target region, the first set of primers selected from the group consisting of SEQ ID NO: 3, SEQ ID NO: 4, SEQ ID NO: 8, SEQ ID NO: 9, SEQ ID NO: 13, SEQ ID NO: 14, SEQ ID NO: 30, and SEQ ID NO: 31;
   subjecting the amplified DNA after the first PCR to a second PCR using the second set of primers corresponding to the target region, the second set of primers selected from the group consisting of SEQ ID NO: 5, SEQ ID NO: 6, SEQ ID NO 10, SEQ ID NO: 11, SEQ ID NO: 15, SEQ ID NO: 16, SEQ ID NO: 32, and SEQ ID NO: 33; and
   subjecting the amplified DNA after the second PCR to denaturing gradient gel electrophoresis,
   wherein the annealing positions of the second set of primers are located inside the annealing positions of the first set of primers relative to the target region.

2. The method according to claim 1, wherein one primer from the second set of primers has a GC-clamp sequence at its 5' side.

3. The method according to claim 1, wherein the density gradient of the denaturing gradient gel is limited to a density gradient of a denaturing agent in the gel comprising acrylamide and the denaturing agent.

* * * * *